United States Patent
Ostrowski et al.

(10) Patent No.: US 11,499,516 B2
(45) Date of Patent: Nov. 15, 2022

(54) METHODS AND SYSTEMS FOR AN ADAPTIVE STOP-START INHIBITOR

(71) Applicant: Ford Global Technologies, LLC, Dearborn, MI (US)

(72) Inventors: David Alfred Ostrowski, Northville, MI (US); Sanjay Abhyankar, Dearborn, MI (US); Leopoldo Urbina, Álvaro Obregón (MX); Sheida Malekpour, Dearborn, MI (US); Christopher Leon Jones, Detroit, MI (US); David Michael Herman, Oak Park, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 85 days.

(21) Appl. No.: 17/089,566

(22) Filed: Nov. 4, 2020

(65) Prior Publication Data
US 2022/0136474 A1 May 5, 2022

(51) Int. Cl.
*F02N 11/08* (2006.01)
*G06N 3/08* (2006.01)
(Continued)

(52) U.S. Cl.
CPC .......... *F02N 11/0822* (2013.01); *A61B 5/024* (2013.01); *A61B 5/165* (2013.01);
(Continued)

(58) Field of Classification Search
CPC ............. F02N 11/0822; F02N 11/0837; F02N 2200/105; A61B 5/024; A61B 5/165;
(Continued)

(56) References Cited

U.S. PATENT DOCUMENTS 6,735,515 B2   5/2004   Bechtolsheim et al.
9,045,132 B1   6/2015   Zhao et al.
(Continued)

FOREIGN PATENT DOCUMENTS

WO   2015178838 A1   11/2015
WO   2017085527 A1   5/2017

OTHER PUBLICATIONS

Rakshit, R. et al., "Emotion Detection and Recognition Using HRV Features Derived from Photoplethysmogram Signal," Proceedings of the 2nd workshop on Emotion Representations and Modelling for Companion Systems, (ERM4CT'16), Tokyo, Japan, Nov. 2016, 6 pages.

*Primary Examiner* — Joseph J Dallo
(74) *Attorney, Agent, or Firm* — Vincent Mastrogiacomo; McCoy Russell LLP

(57) ABSTRACT

Methods and systems are provided for selectively inhibiting a stop-start controller of a vehicle based on a predicted anxiety of a driver of the vehicle on a road segment that includes one or more road attributes associated with increased levels of anxiety. In one example, selectively inhibiting a stop-start controller of a vehicle based on a predicted anxiety of a driver of the vehicle includes determining a driver classification for a driver operating the vehicle; predicting an anxiety level of the driver at an upcoming traffic condition, based on the driver classification; and selectively inhibiting an upcoming engine idle-stop event based on the predicted anxiety level of the driver.

20 Claims, 12 Drawing Sheets

(51) Int. Cl.
*G06F 16/29* (2019.01)
*G06F 16/23* (2019.01)
*G01S 13/931* (2020.01)
*G01S 19/01* (2010.01)
*G10L 25/63* (2013.01)
*G06K 9/62* (2022.01)
*A61B 5/18* (2006.01)
*A61B 5/16* (2006.01)
*A61B 5/00* (2006.01)
*A61B 5/024* (2006.01)
*G06V 20/56* (2022.01)
*G06V 20/59* (2022.01)

(52) U.S. Cl.
CPC .............. *A61B 5/18* (2013.01); *A61B 5/7267* (2013.01); *A61B 5/7275* (2013.01); *F02N 11/0837* (2013.01); *G01S 13/931* (2013.01); *G01S 19/01* (2013.01); *G06F 16/2379* (2019.01); *G06F 16/29* (2019.01); *G06K 9/628* (2013.01); *G06K 9/6218* (2013.01); *G06N 3/08* (2013.01); *G06V 20/588* (2022.01); *G06V 20/597* (2022.01); *G10L 25/63* (2013.01); *F02N 2200/105* (2013.01)

(58) Field of Classification Search
CPC ....... A61B 5/18; A61B 5/7267; A61B 5/7275; G01S 13/931; G01S 19/01; G06F 16/2379; G06F 16/29; G06K 9/6218; G06K 9/628; G06N 3/08; G06V 20/588; G06V 20/597; G10L 25/63
See application file for complete search history.

(56) References Cited

U.S. PATENT DOCUMENTS

| | | | |
|---|---|---|---|
| 9,371,766 | B2 | 6/2016 | Wang et al. |
| 9,898,928 | B1 | 2/2018 | Payne |
| 2013/0053090 | A1 | 2/2013 | Chaudhri et al. |
| 2014/0088858 | A1 | 3/2014 | Stefan et al. |
| 2014/0343830 | A1 | 11/2014 | Elwart et al. |
| 2016/0001781 | A1* | 1/2016 | Fung ............. G16H 50/20 701/36 |
| 2018/0093650 | A1 | 4/2018 | Payne et al. |
| 2018/0118189 | A1 | 5/2018 | Payne |
| 2018/0120119 | A1 | 5/2018 | Payne |
| 2019/0046055 | A1* | 2/2019 | Gañán Calvo ........ A61B 5/316 |
| 2021/0107496 | A1* | 4/2021 | Oboril ............ B60W 60/00253 |

\* cited by examiner

METHODS AND SYSTEMS FOR AN ADAPTIVE STOP-START INHIBITOR

FIELD

The present description relates generally to methods and systems for controlling engine idle stop and restart activities on a vehicle with an auto-stop feature, and more specifically, to controlling engine idle stop and restart activities based on a predicted emotional state of a driver.

BACKGROUND/SUMMARY

A hybrid vehicle may be equipped with an engine auto-stop system. An engine auto-stop system shuts down the engine during certain periods of vehicle operation to conserve fuel. For example, engine auto-stop may be engaged when the vehicle is stopped at a traffic light or in a traffic jam rather than permitting the engine to idle. The engine may be restarted when the driver releases the brake or actuates the accelerator pedal. The engine may also be started, for example, due to loads on the electrical system. Stopping the engine when it is not needed improves fuel economy and reduces emissions.

One challenge posed by engine stop-start systems is that they may cause anxiety in drivers around the potential of not being able to start in situations where drivers are engaged in heavy traffic, particularly in scenarios where there are (high-anxiety) left-turn scenarios and successive stopping conditions (four-way stop intersections/multiple yield scenarios). One solution that has been implemented is a manual override, whereby a driver can manually disable a stop-start system. This has resulted in some customers using stop-start functionality on a very selective basis, with a corresponding reduction in fuel efficiency. Another solution is to automatically calibrate the stop-start system based on a condition of the vehicle or the driver. For example, as shown by Ford et al in U.S. Patent Application Publication No. 2014/0343830A1, the stop-start system may be automatically enabled or disabled based on an emotional state of the driver, as determined by a machine learning system that takes as input images of the driver's face via an internal dashboard camera.

However, inventors herein have recognized potential issues with automatic calibration of the stop-start feature. For example, video data collected via an internal camera may not provide an accurate indication of the driver's emotional state, and current methods of automatic feature calibration do not take into account a driver's driving history, profile, or road attribute information generated by an internal navigation system, which could be used to provide a more robust estimate of a driver's level of anxiety. Additionally, current methods of automatic feature calibration cannot predict a driver's emotional state in advance, in order to prevent or avoid conditions that make the driver anxious (e.g., inhibiting the stop-start feature, suggesting a different route, calculating a different optimal route, etc.). Further, current methods do not leverage collective information from connected vehicle fleets, which can support identification of scenarios before a driver has encountered a situation for the first time.

In one example, the issues described above may be addressed by a method for a controller of a vehicle, comprising determining a driver classification for a driver operating the vehicle; predicting an anxiety level of the driver at an upcoming traffic condition, based on the driver classification; and selectively inhibiting an upcoming engine idle-stop event based on the predicted anxiety level of the driver. Predicting an anxiety level of the driver may include training a driver classification model to classify the driver into one of a plurality of driver classifications; training an anxiety classification model to classify an anxiety level of the driver based on data received from a dashboard camera, microphone, and other sensors of the vehicle and/or worn by the driver; and assigning an anxiety classification to a road segment for each driver classification of the plurality of driver classifications. By anticipating driving conditions where the driver may experience anxiety during a traffic stop, an idle-stop event may be selectively inhibited until the vehicle reaches a road segment associated with less anxiety.

As an example, an upcoming road segment of the vehicle may be defined from look-ahead data from one or more sources, including an external camera of the vehicle, an onboard navigation system, and/or sensors of another vehicle within a vehicle-to-vehicle (V2V) network formed between vehicles within a threshold distance of a target vehicle. A driver category may be assigned to the driver by the driver classification model. A neural network may be trained to classify the upcoming road segment to road segment category. A predicted anxiety may be associated with the road segment, for the driver category of the driver, based on emotional data collected from a plurality of drivers via internal sensors of the vehicles of the drivers as various road attributes are encountered. Based on the predicted anxiety of the driver on the upcoming road segment (e.g., corresponding to the driver category), and anxiety data for the upcoming road segment retrieved from a lead network of vehicles, an upcoming idle-stop event may be selectively inhibited, or a different route may be suggested, based on the predicted anxiety level of the driver. In this way, an optimal strategy may be devised that continuously monitors upcoming road segments to suggest low-anxiety routes and to mitigate driver anxiety at traffic stops by inhibiting an idle-stop event.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
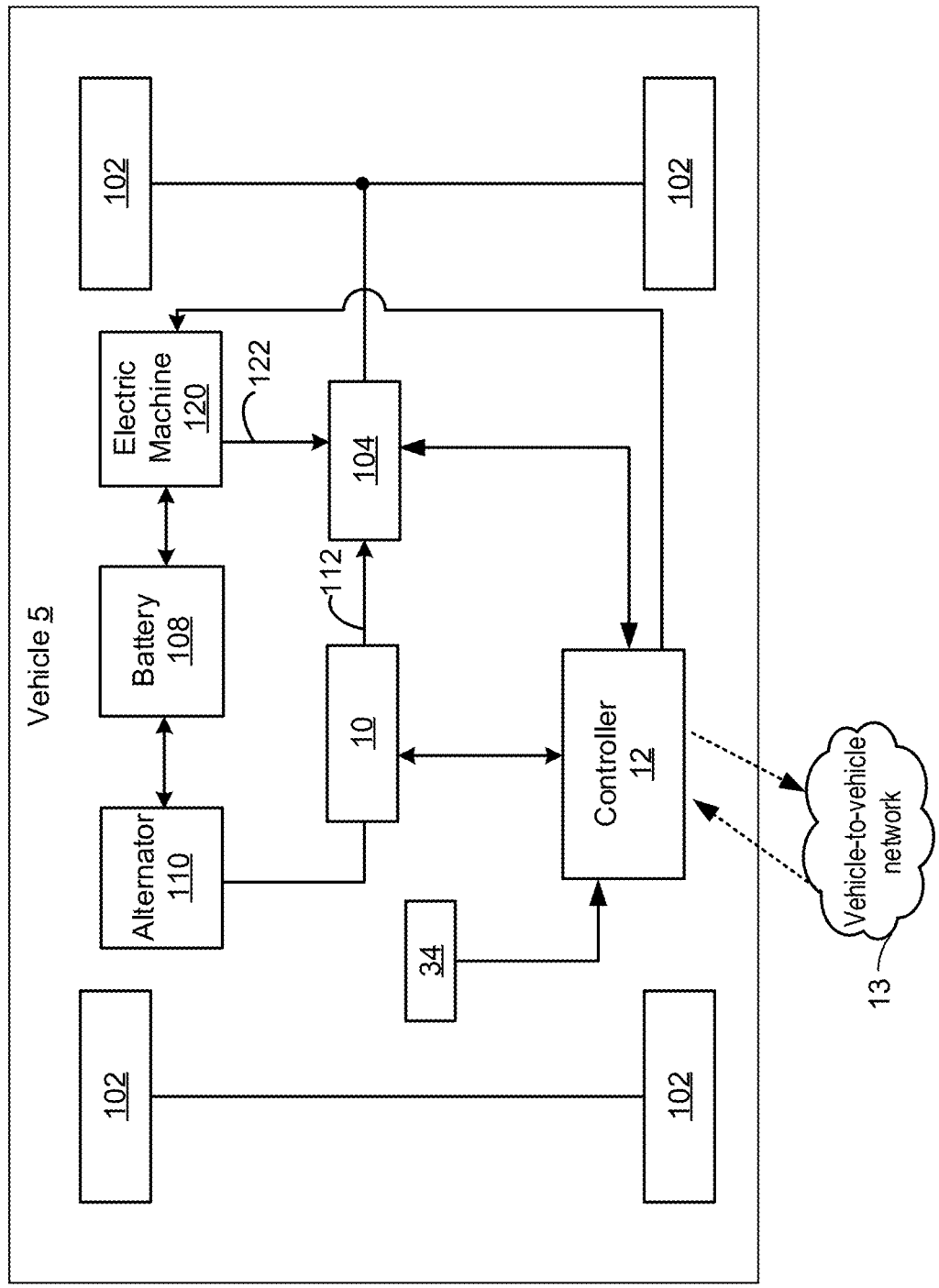
FIG. 1 shows a schematic depiction of a vehicle system.

The following description relates to systems and methods for selectively inhibiting a stop-start controller of a vehicle based on an anxiety level of a driver of the vehicle. The anxiety level of the driver at an upcoming road segment may be predicted based on a driver classification and look-ahead road attribute information determined from sensors of the vehicle and/or other vehicles in a vehicle fleet with which it may be in communication, in conjunction with stored anxiety information retrieved from a navigational database.

As mentioned herein, inhibiting a stop-start controller of a vehicle with an engine auto-stop system refers to preventing the stop-start controller from automatically shutting off an engine of the vehicle in response to a set of operating conditions having been met, until a threshold time has elapsed and/or a change in the operating conditions occurs. In one example, the set of operating conditions includes an engine idle situation when the vehicle is in a stopped condition at a location of a traffic stop, and the change in operating conditions includes an engagement of one or more gears of a transmission of the vehicle as the vehicle proceeds through the traffic stop. For example, when the stop-start controller is enabled, the stop-start controller may automatically shut off the engine when the vehicle is waiting at a stoplight to increase a fuel efficiency of the vehicle. However, if the stop-start controller is inhibited prior to reaching the stoplight, the stop-start controller may be disabled such that the engine is not automatically shut off when the vehicle is waiting at the stoplight. After one or more gears of the engine are engaged and the vehicle moves through the stoplight and/or a threshold time passes (e.g., 10 seconds), inhibition of the stop-start controller may end, whereby the stop-start controller is enabled.

The classification of the driver may be determined by a driver classification model. In one example, the driver classification model takes as input vehicle data and historical performance data of a plurality of drivers, and uses a clustering algorithm to identify one or more natural peer groupings. A neural network is trained to map new drivers to the one or more natural peer groupings.

The upcoming road segment may be classified to a predicted anxiety by an anxiety classification model. Further, each of the one or more natural peer groupings (e.g., driver categories) may be assigned an anxiety classification model, whereby for a road segment, different anxiety classifications may be generated for each driver category.

In one example, the anxiety classification models are constructed from driver data from a plurality of drivers, where the driver data may be used to estimate an emotional state of the driver on a road segment. The driver data may include video images of a facial expression of the driver, audio recordings from a microphone installed in the vehicle cabin, physiological data collected from an IOT device (e.g., a smart watch, a fitness tracker, etc.), ECG data from an ECG sensing device (e.g., an Emotiv® device), or data from other sensors of the vehicle. A neural network is trained to output a predicted level of anxiety of a new driver on the segment, based on a driver category of the new driver.

For example, the anxiety classification may be a numeric value on a scale of 1 to 10 where 10 represents a high level of anxiety. For one driver category, a first road segment that includes a 4-way stop may have an anxiety classification of 7, indicating that a driver of the driver category may experience higher than average anxiety on the first road segment as a result of a multiple yield scenario. Alternatively, a second road segment that comprises a straight section of road with no turns may have an anxiety classification of 1 for the same driver category, indicating that a driver of the driver category may experience lower than average anxiety on the second road segment. In another example, a different scale may be used, or anxiety classifications may not be based on a numeric scale. It should be appreciated that the examples provided herein are for illustrative purposes, and other types of scales or classifications may be used without departing from the scope of this disclosure.

Figure 2:
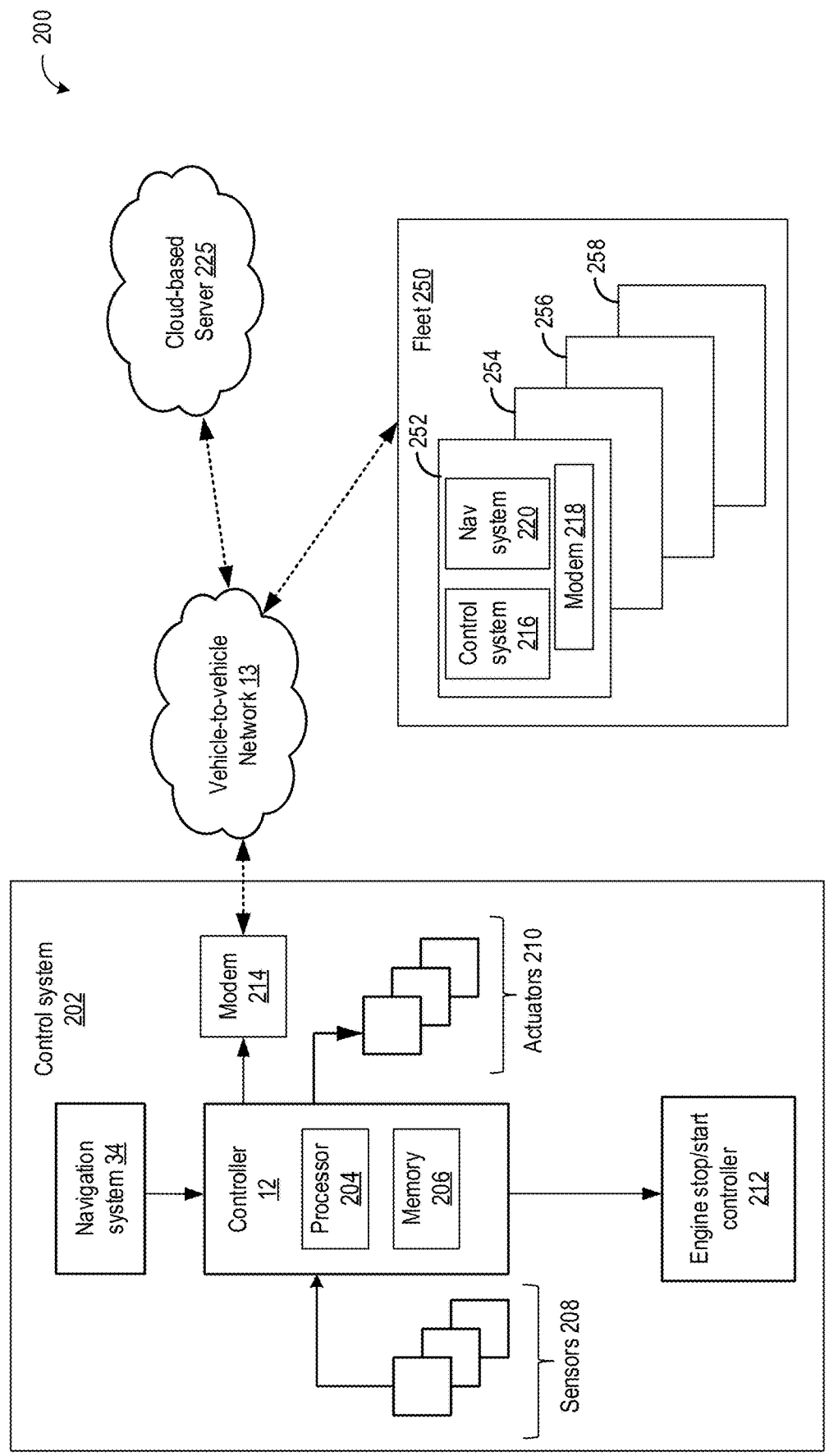
FIG. 2 shows an example embodiment of a vehicle control system, in communication with an external network and a fleet of vehicles.
Figure 3A:
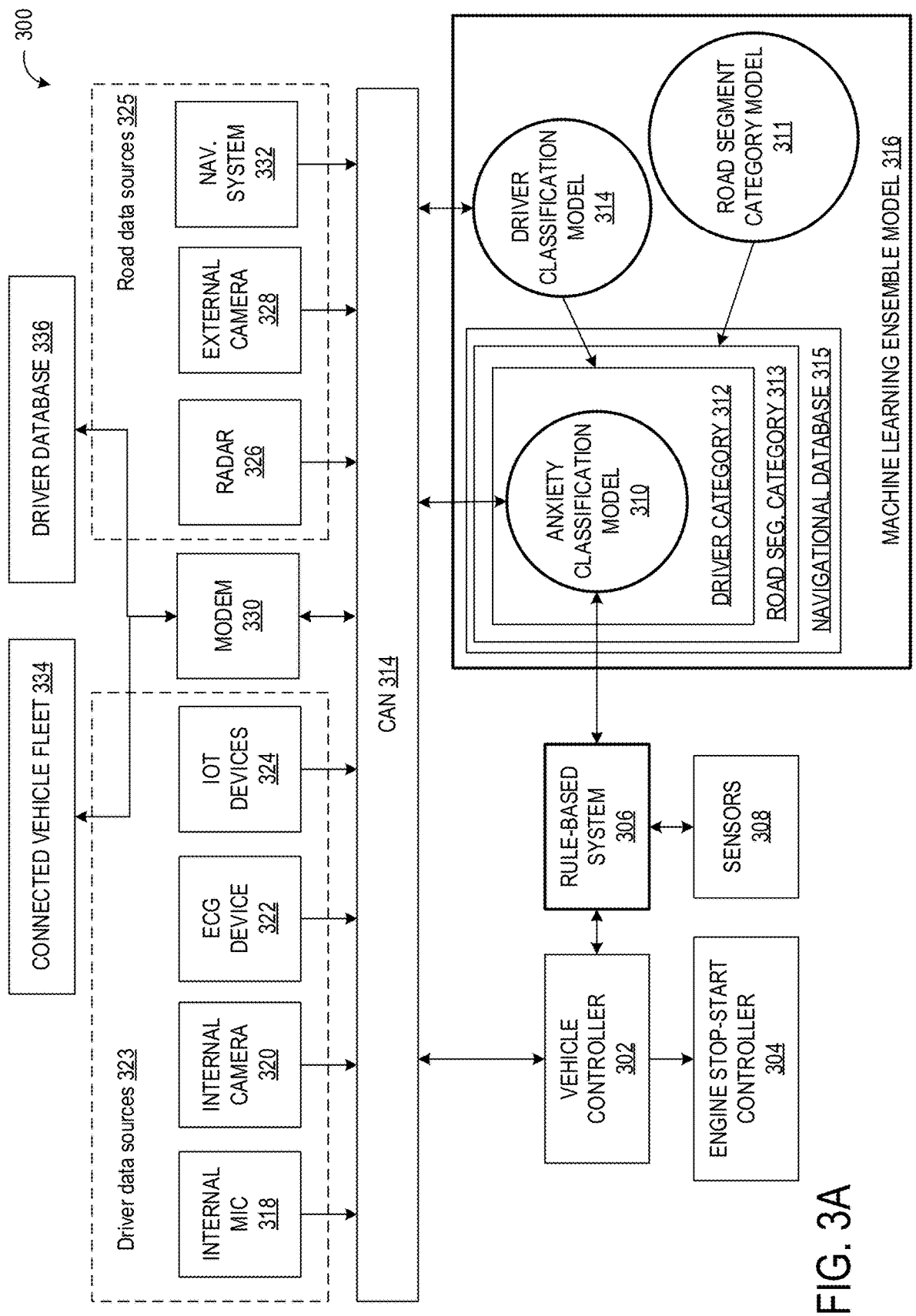
FIG. 3A shows a schematic depiction of a vehicle control sub-system for assigning an anxiety classification to a road segment.

An example vehicle system including a hybrid drive is depicted in FIG. 1. The vehicle system may include a control system, which may be in communication with a fleet of vehicles via a vehicle-to-vehicle network, as shown in FIG. 2. A controller of the control system may receive inputs from a plurality of devices, sensors, and systems to determine whether to selectively inhibit an engine stop-start controller, as depicted in FIG. 3A. A neural network may be trained to predict a level of anxiety of the driver based on driver performance data, driver emotion data, and look-ahead road attribute information, in accordance with the system shown in FIG. 4. FIG. 5 describes an exemplary overall procedure for selectively inhibiting an engine stop-start controller, based on a driver classification model, an anxiety classification model, and a road segment classification model. The road segment classification model may be trained according to the procedure described in FIG. 10. The anxiety classification model may be created based on the procedure described in FIG. 6. A dashboard camera may be used to detect a facial expression of the driver, as shown in FIG. 11, which may be an input into the anxiety classification model. The trained driver classification and anxiety classification models may be used to predict a future driver emotion according to the procedures described in FIGS. 7 and 8, which may be used by a rule-based system, in conjunction with sensor data of the vehicle, to selectively enable or disable stop-start functionality of the vehicle system according to the procedure described in FIG. 9.

Referring now to FIG. 1, an example vehicle 5 is shown. In some examples, vehicle 5 may be a hybrid vehicle with multiple sources of torque available to one or more vehicle wheels 102. In other examples, vehicle 5 is a conventional vehicle with only an engine, or an electric vehicle with only electric machine(s). In the example shown, vehicle 5 includes an internal combustion engine 10 and an electric machine 120. Electric machine 120 may be a motor or a motor/generator. Electric machine 120 may be configured to utilize or consume a different energy source than engine 10. For example, engine 10 may consume a liquid fuel (e.g., gasoline) to produce an engine output while electric machine 120 may consume electrical energy to produce a motor output. As such, the vehicle 5 may be referred to as a hybrid electric vehicle (HEV).

In a non-limiting embodiment, electric machine 120 receives electrical power from a battery 108 to provide torque to vehicle wheels 102. Engine 10 and electric machine 120 are connected to the vehicle wheels 102 via a transmission 104. Transmission 104 may be a gearbox, a planetary gear system, or another type of transmission.

Vehicle 5 may utilize a variety of different operational modes depending on operating conditions encountered. Some of these modes may enable engine 10 to be maintained in an off state where combustion of fuel at the engine is discontinued. For example, under select operating conditions, electric machine 120 may propel the vehicle via transmission 104 as indicated by arrow 122 while engine 10 is deactivated. The select operating conditions may include a stopped condition, wherein the engine 10 may be maintained in an off state while the vehicle 5 is not moving. When the vehicle 5 begins to accelerate, the vehicle 5 may be propelled by electric machine 120, or engine 10 may be switched to an on state and may propel the vehicle 5.

During other operating conditions, electric machine 120 may be operated to charge an energy storage device such as the battery 108. For example, electric machine 120 may receive wheel torque from transmission 104 as indicated by arrow 122 where the motor may convert the kinetic energy of the vehicle to electrical energy for storage at battery 108. Thus, electric machine 120 can provide a generator function in some embodiments. However, in other embodiments, alternator 110 may instead receive wheel torque from transmission 104, or energy from engine 10, where the alternator 110 may convert the kinetic energy of the vehicle to electrical energy for storage at battery 108.

During still other operating conditions, engine 10 may be operated by combusting fuel received from a fuel system (not shown in FIG. 1). For example, engine 10 may be operated to propel the vehicle via transmission 104 as indicated by arrow 112 while electric machine 120 is deactivated. During other operating conditions, both engine 10 and electric machine 120 may each be operated to propel the vehicle via transmission 104 as indicated by arrows 112 and 122, respectively. A configuration where both the engine and the motor may selectively propel the vehicle may be referred to as a parallel type vehicle propulsion system. Note that in some embodiments, electric machine 120 may propel the vehicle via a first drive system and engine 10 may propel the vehicle via a second drive system.

Operation in the various modes described above may be controlled by a controller 12. For example, controller 12 may identify and/or control the amount of electrical energy stored at the energy storage device, which may be referred to as the state of charge (SOC). In addition, controller 12 may receive data from a navigation device 34 such as a global positioning system (GPS) and/or a vehicle-to-vehicle (V2V) network such as an off-board V2V network 13. Controller 12 will be described below in more detail in reference to FIG. 2.

Turning to FIG. 2, a schematic depiction 200 of additional components of vehicle 5 is shown. The vehicle 5 may include a control system 202. Control system 202 is shown receiving information from a plurality of sensors 208 and sending control signals to a plurality of actuators 210. As one example, sensors 208 may include one or more of an exhaust gas sensor, an upstream and/or downstream temperature sensor, an airflow sensor, a pressure sensor, an air/fuel ratio sensor, a catalyst temperature sensor, and/or a composition sensor, which may be coupled to various locations in the vehicle 5. The actuators may include a fuel injector, a throttle, one or more valves of an engine or fuel system, etc. It should be appreciated that the examples provided herein are for illustrative purposes and other types of sensors and/or actuators may be included without departing from the scope of this disclosure.

The control system 202 may include a controller 12. The controller 12 may include a processor 204. The processor 204 may generally include any number of microprocessors, ASICs, ICs, etc. The controller 12 may include a memory 206 (e.g., FLASH, ROM, RAM, EPROM and/or EEPROM) that stores instructions that may be executed to carry out one more control routines. As discussed herein, memory includes any non-transient computer readable medium in which programming instructions are stored. For the purposes of this disclosure, the term tangible computer readable medium is expressly defined to include any type of computer readable storage. The example methods and systems may be implemented using coded instruction (e.g., computer readable instructions) stored on a non-transient computer readable medium such as a flash memory, a read-only memory (ROM), a random-access memory (RAM), a cache, or any other storage media in which information is stored for any duration (e.g. for extended period time periods, permanently, brief instances, for temporarily buffering, and/or for caching of the information). Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include any other medium which can be used to store the desired electronic format of information and which can be accessed by the processor or processors or at least a portion of a computing device.

In general, controller 12 receives input from various vehicle sensors 208 that indicate engine, transmission, electrical and climate states. A vehicle speed may also be communicated to controller 12 through a speed sensor. The controller 12 may receive input from an accelerator and/or brake pedal, and a navigation system 34 that provides information that may be used to predict and determine durations of upcoming vehicle stop events. The navigation system 34 may receive information from the vehicle speed sensor, GPS, traffic flow data, local gradient maps, etc. In one configuration, the navigation system 34 may be an in-vehicle GPS system. In another configuration, the navigation system 34 may comprise a location-enabled mobile device, such as a smart phone or standalone GPS unit.

The controller 12 may receive input data from the various sensors 208, process the input data, and trigger the actuators 210 in response to the processed input data based on instructions stored in the memory 206. For example, the controller 12 may receive input data from an air/fuel ratio sensor indicating that an air/fuel ratio of the engine is low, and as a result, the controller 12 may command a fuel injector to adjust the air/fuel ratio.

The control system 202 may include an engine stop/start controller 212 that includes appropriate start/stop logic and/or controls for controlling an auto-stop system of an engine (e.g., engine 10 of the vehicle 5 of FIG. 1). An engine auto-stop system may shut down the engine during certain periods of vehicle operation to conserve fuel. For example, the auto-stop system may shut the engine off during engine idle conditions where the engine is not required for propulsion or other purposes. The auto-stop system may then restart the engine when required for propulsion or other purposes. By disabling the engine when not in use, overall fuel consumption is reduced.

The engine stop/start controller 212 may be configured to initiate an auto-stop or auto-start of the engine during various operating conditions. As the vehicle comes to a stop, for example, the engine stop/start controller 212 may issue a command to begin the process to stop the engine, thus preventing the alternator or integrated starter generator from providing electric current to the electrical loads. The battery may provide electric current to the electrical loads while the engine is stopped. As the brake pedal is disengaged (and/or the accelerator pedal is engaged) after an engine auto-stop, the engine stop/start controller 212 may issue a command to begin the process to start the engine, thus enabling the alternator or integrated starter generator to provide electric current to the electrical loads.

The control system 202 may include a modem 214. Via the modem 214, the controller 12 may communicate with other vehicle controllers over the V2V network 13 with a cloud-based server 225 and a fleet of vehicles 250 including a vehicle 252, a vehicle 254, a vehicle 256, and a vehicle 258. In some examples, the controller 12 may communicate with other vehicle controllers over the V2V network 13 in real time, while in other examples, the other vehicle controllers may transmit data to the cloud-based server 225 to be accessed later by the controller 12. In an embodiment, the V2V network is a controller area network (CAN), which may be implemented using any number of communication protocols generally known. Using the modem 214, the vehicle 5 may retrieve data from the vehicles 252, 254, 256, and 258 via the V2V network 13. For example, the data may include road condition data from a vehicle traveling ahead of the vehicle 5 on a route of the vehicle 5, whereby the controller 12 may adjust one or more system settings of the vehicle 5 in anticipation of the upcoming road condition.

The cloud-based server 225 may include one or more databases, such as, for example, a driver database that stores driving data of a plurality of drivers of the fleet 250. For example, the driving data may include a driver profile, a driver classification, and/or historical performance data for each driver of the plurality of drivers of the fleet 250. The cloud-based server 225 may also include a navigational database, which may include road attribute information such as number of stop lights, number of intersections, etc.

The controller 12 may be able to run an application for connecting to a cloud-based server 225 and/or collecting information for transmission to the cloud-based server 225 and/or receiving information from the cloud-based server 225. For example, the application may retrieve information gathered by vehicle systems/sensors, input devices, devices such as a mobile device connected via a Bluetooth® link, and the like, and send the information gathered to the cloud-based server 225 for processing. The navigation system 34 may determine a current location of the vehicle 5, which may be transmitted to the cloud-based server 225 from the vehicle 5 to be used in the processing of the information gathered. In one example, the vehicle 5 may transmit emotional data of a driver of the vehicle 5 (e.g., images of facial expressions, audio recordings of the driver, etc.) corresponding to a location of the vehicle 5 to the cloud-based server 225, from which an application running on the cloud-based server 225 may determine an emotional state of the driver. In some examples, the emotional state of the driver is transmitted back to the vehicle 5. In one example, the emotional data of the driver is aggregated with emotional data of other drivers of the vehicles 252, 254, 256, and 258 of fleet 250, to generate anxiety classifications for road segments with similar attributes as encountered at the location of the vehicle 5.

In one example, the vehicles 252, 254, 256, and 258 of fleet 250 may each be similar in make and model to the vehicle 5. In other examples, the vehicles 252, 254, 256, and 258 of fleet 250 may be vehicles within a threshold distance of vehicle 5. In one example, the threshold distance may be defined as a distance within which one or more road conditions experienced by the vehicles 252, 254, 256, and 258 are considered to be similar to those of vehicle 5. In another example, the threshold distance may be a distance that the vehicle 5 can cover in a pre-established duration (e.g., 1 minute), whereby a road attribute located at the threshold distance is reached in 1 minute. Each of the vehicles 252, 254, 256, and 258 of fleet 250 may include a control system 216, a modem 218, and a navigation system 220, which may be the same as or similar to the control system 202, navigation system 34, and a modem 214 of the vehicle 5. The on-board controllers in the vehicles 252, 254, 256, and 258 may communicate with each other and to the on-board controller in vehicle 5 via their respective modem 218, navigation system 220, and/or via other forms of V2V technology.

In one example, the fleet 250 is within a threshold radius of the vehicle 5, and the road conditions encountered by each of the vehicles 252, 254, 256, and 258 of the fleet may be similar to the conditions experienced by the vehicle 5. A statistical weighted average of an estimate retrieved from each vehicle of the remote fleet of vehicles may be used by the control system 202 of vehicle 5 to determine a future driving condition of the vehicle 5. For example, when the average vehicle speed of fleet 250 is lower than a threshold (e.g., 5 mph), and has continued to remain under the threshold for a certain duration, it may be determined that the vehicle 5 may encounter slow moving traffic or stopped vehicles in the future. As such, the navigation system 34 may be able to determine the traffic conditions, and further estimate a time for which the condition may persist. In this way, the vehicle 5 may communicate with remote sources (e.g., an external network cloud, other vehicles, a navigational database of road attributes) using one or multiple technologies e.g., wireless communication, navigation system and V2V.

Various kinds of data may be exchanged between the vehicle 5 and the remote sources. The data may include a preview of upcoming traffic conditions, types of roads, accidents or construction along the route, stalled or stopped vehicles, number of traffic lights, and the like, all of which may be received concurrently or sequentially. For example, when a long stretch of downward sloping road is detected, it may indicate a coasting condition. Information relayed within the vehicle network may include one or more of vehicle speed, an average speed of vehicles within the vehicle network, duration for which the speed is maintained, and the like. For example, a congestion in traffic may be deduced from an average speed of one or more vehicles, a high braking rate of one or more vehicles, and/or a close proximity of vehicles (e.g., detecting tail lights, etc.). In other examples, higher average speeds maintained for longer duration and braking rates that are low may indicate cruising conditions. In still other examples, an extended idle condition may be inferred when the average speed of the vehicles in the network is near zero for a long period of time.

In one example, the data exchanged includes road attribute data (e.g., a presence of an intersection, stoplight, etc.), which the vehicle 5 uses to determine whether to selectively inhibit the engine stop-start controller 212. In other examples, the data includes emotional data of one or more drivers of one or more of the vehicles 252, 254, 256, and 258. In some examples, the emotional data includes one or more of an image of a facial expression of a driver, an audio recording of the driver, a vital sign of the driver recorded via a device worn by the driver, and a pattern of neural activity of the driver captured via an ECG device. In other examples, the emotional data includes an anxiety classification of a road segment on which one or more of the vehicles 252, 254, 256, and 258 is traveling.

Turning now to FIG. 3A, an engine stop-start control system 300 of the vehicle 5 is shown. The engine stop-start control system 300 may include elements that are the same as or similar to elements of the control system 202 of FIG. 2 and vehicle 5 of FIG. 1. In particular, the engine stop-start control system 300 includes a vehicle controller 302 that may be the same as or similar to vehicle controller 12 of control system 202 of FIG. 2, and an engine stop-start controller 304 that may be the same as or similar to engine stop-start controller 212 of control system 202 of FIG. 2.

The vehicle controller 302 may selectively inhibit the engine stop-start controller 304 based on an output of a rule-based system 306. The rule-based system 306 may receive as input sensor data from one or more sensors 308 of the vehicle 5. For example, an output of a battery SOC sensor may indicate an SOC of the battery. If the SOC of the battery is below a threshold SOC (e.g., 10%), the rule-based system may disable the stop-start controller 304 based a lack of sufficient charge to shut off the engine during idle. As another example, the rule-based system may disable the stop-start controller 304 if a setting of the vehicle 5 indicates that a driver of the vehicle 5 has selected to manually override an auto-stop system of the vehicle 5. In one example, the rule-based system 306 considers the data received from a plurality of sensors 308 sequentially in accordance with a pre-established hierarchy of conditions under which the stop-start controller 304 is selectively inhibited. For example, the rule-based system 306 may first make a first determination that the battery SOC is above the threshold SOC, and subsequently make a second determination that the vehicle is stopped, and as a result of both of the first determination and the second determination, output an instruction to inhibit the stop-start controller 304. In other examples, the rule-based system 306 considers the data received from the plurality of sensors 308 non-sequentially (e.g., where the first determination may be made prior to the second determination, or the second determination may be made prior to the first determination).

An additional input to the rule-based system 306 may include an output of a machine learning ensemble model 316, which may be a predicted level of anxiety of a driver of the vehicle 5 on an upcoming road segment of a route on which the driver is operating the vehicle 5. The machine learning ensemble model 316 may include a driver classification model 310, a road segment category model 311, and a navigational database 315. The navigational database 315 may include a plurality of road segment categories, where each road segment category of the plurality of road segment categories includes a plurality of driver categories, and where each driver category includes an anxiety classification model associated with the driver category. FIG. 3A depicts one anxiety classification model 310, corresponding to one driver category 312 of the plurality of driver categories that correspond to one road segment category 313. In other words, the anxiety classification model 310 is an anxiety model selected for the driver of the vehicle on an upcoming road segment, based on the driver category 312 of the driver determined by the driver classification model 314, that is associated with the road segment category 313, which is the road segment category returned by the road segment category model 311 as the closest match to the upcoming road segment. The structure of the navigational database is described in greater detail below in relation to FIG. 3B.

Figure 3B:
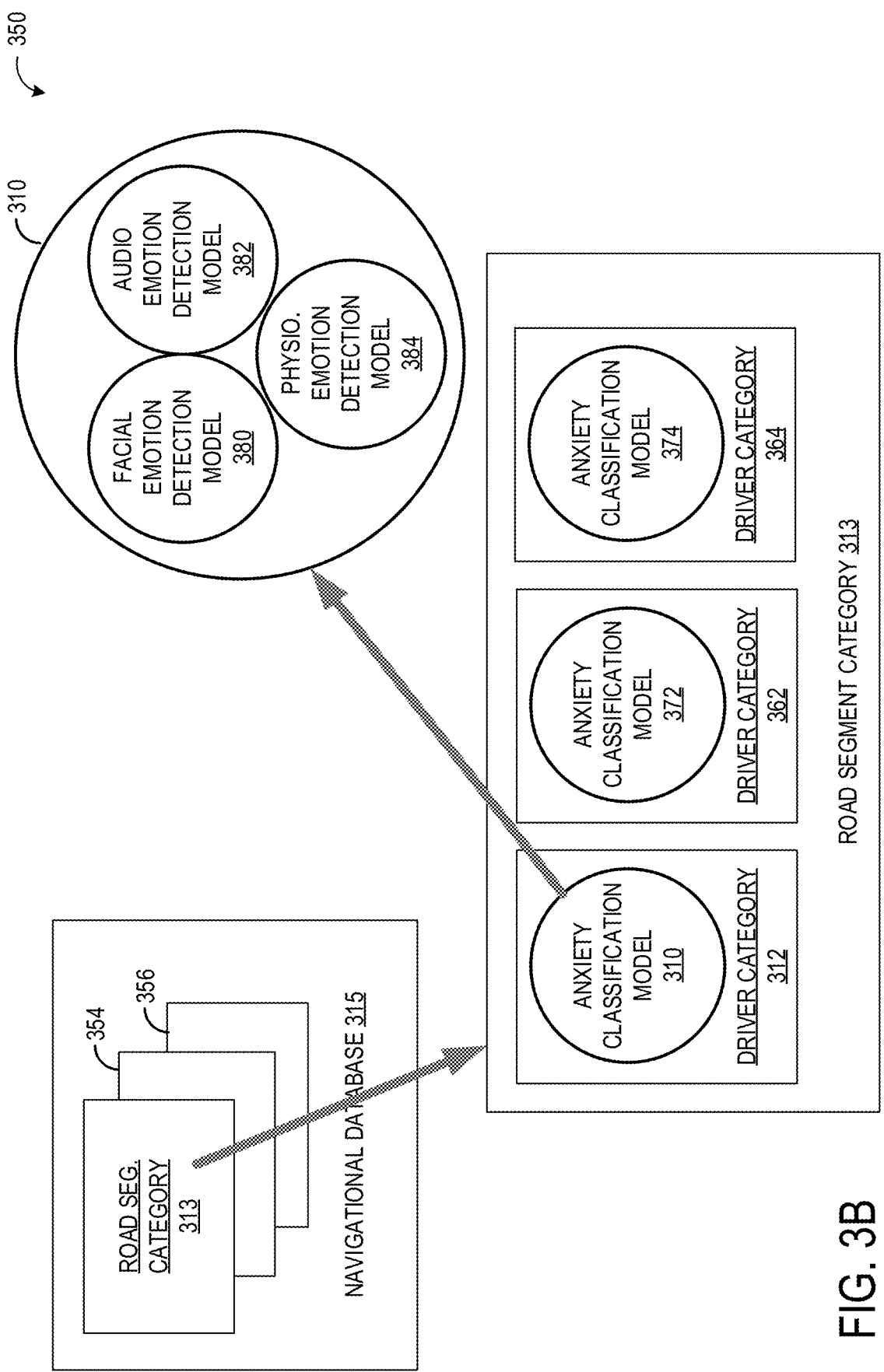
FIG. 3B shows an exploded view of a navigational database.

Turning briefly to FIG. 3B, an exploded view 350 of the navigational database 315 is shown, which includes a plurality of road segment categories 313, 354, and 356. Each road segment category of the road segment categories 313, 354, and 356 includes a plurality of anxiety classification models 310, 372, and 374, where each anxiety classification model of the anxiety classification models 310, 372, and 374 produces an anxiety classification for the parent road segment category based on one of a plurality of driver categories 312, 362, and 364. Further, each anxiety classification model of the anxiety classification models 310, 372, and 374 may include one or more emotion detection models, such as a facial emotion detection model 380, an audio emotion detection model 382, and/or a physiological emotion detection model 384, whereby the anxiety classification outputted for the parent road segment category and the driver category is a function of the outputs of the facial emotion detection model 380, the audio emotion detection model 382, and/or the physiological emotion detection model 384. In one example, the anxiety classification outputted for the parent road segment category is a weighted average of the outputs of the facial emotion detection model 380, the audio emotion detection model 382, and/or the physiological emotion detection model 384. The development of the emotion detection models is described in greater detail below in relation to FIG. 6.

Returning to FIG. 3A, the predicted level of anxiety of the driver outputted by the machine learning ensemble model 316 may be in the form of an anxiety classification generated by a selected anxiety classification model 310, where the selected anxiety classification model 310 is the anxiety classification model that corresponds to the driver category 312 of the driver outputted by the driver classification model 314. The creation of the driver classification model is described in greater detail below in relation to FIG. 5.

In one example, the anxiety classification is a numeric value indicating a predicted level of anxiety of the driver. For example, the selected anxiety classification model 310 may output a predicted level of anxiety of the driver of 2 on a scale of 1 to 10, indicating that a low level of anxiety is predicted for the driver while operating the vehicle 5 on the upcoming road segment. Alternatively, the selected anxiety classification model 310 may output a predicted level of anxiety of the driver of 8 on a scale of 1 to 10, indicating that a high level of anxiety is predicted for the driver while operating the vehicle 5 on the upcoming road segment. Further, for an upcoming road segment, the anxiety classification model 310 may output a first predicted level of anxiety for a first driver of vehicle 5 and a second predicted level of anxiety for a second driver of vehicle 5, where the first predicted level of anxiety corresponds to a first driver classification and the second predicted level of anxiety corresponds to a second driver classification. The development of the anxiety classification model 310 is described below in greater detail in reference to FIG. 6.

In an embodiment, each anxiety classification model of the anxiety classification models 310 may generate an anxiety classification of an upcoming road segment for the corresponding driver category 312, based on data received from a plurality of devices, sensors, and systems of vehicle 5, including data from one or more driver data sources 323 and/or one or more road data sources 325. More specifically, inputs to the anxiety classification models 310 in the form of driver data from a plurality of driver data sources 323 may include, for a driver operating the vehicle 5, an output of an internal microphone 318 installed inside the vehicle 5, in the form of an audio recording of the driver; an output of an internal camera 320 installed inside the vehicle 5 (e.g., a dashboard cam), in the form of an image of a facial expression of the driver; the output of a wearable ECG sensing device 322 worn by the driver, in the form of a representation of neural activity; and/or an output of one or more IOT devices 324 worn by the driver, in the form of physiological data of the driver (e.g., heart rate, galvanic skin response, blood pressure, etc.). In one example, the one or more IOT devices 324 may include a smart watch or fitness tracker.

During construction of the anxiety classification models 310, the data of a driver received from the driver data sources 323 may be applied to the selected anxiety classification model 310 associated with the driver category of the driver, and not to other anxiety classification models 310 associated with other driver categories. For example, a driver category of the driver may first be obtained from the driver classification model 314, and the data of the driver may subsequently be used to construct or reinforce the anxiety classification model 310 associated with the driver category.

Inputs to the anxiety classification models 310 in the form of road attribute data from a plurality of road data sources 325 may include an output of a radar device 326, which may be used to link coordinates for reference to external sources of navigational/road attribute data; an output of an external camera 328, in the form of images of road attributes of a road segment or an upcoming road segment (herein, "look-ahead" road attribute information); and/or an output of an onboard navigational system 332, in the form of a set of global positioning system (GPS) coordinates indicating a location of the vehicle 5. In addition, an output of a modem 330 may be an input to the anxiety classification models 310, in the form of road segment and/or road condition data and/or traffic data received from one or more controllers of vehicles of a connected vehicle fleet 334 (including location data from the onboard navigation systems of the vehicles of the connected vehicle fleet 334). Further, emotional data of one or more drivers of the vehicles of the connected vehicle fleet 334 may be received, such as an anxiety of a driver when encountering a road attribute along a route of the vehicle 5.

For example, a first vehicle of a vehicle fleet (e.g., the vehicle fleet 250 of FIG. 2) and a second vehicle of the vehicle fleet may be traveling along a road, where the first vehicle is ahead of the second vehicle, and where a road attribute encountered by the first vehicle will be encountered by the second vehicle after a period of time (e.g., 1 minute). The second vehicle may determine that the first vehicle is operating on a future route of the second vehicle, and may request data from the first vehicle regarding upcoming road attributes. Upon encountering a stoplight of the route, the first vehicle may transmit to the second vehicle a rode attribute code for a stoplight, thereby indicating that the stoplight will be encountered by the second vehicle after the period of time. In some examples, the second vehicle may also transmit a location of the stoplight (e.g., GPS coordinates). In response to receiving the road attribute code for the stoplight, the second vehicle may adjust one or more driving settings of the second vehicle in anticipation of the stoplight (e.g., selectively inhibit the engine stop-start controller 304 of the vehicle).

Additionally, or alternatively, a first driver of the first vehicle may experience an increased anxiety upon encountering the stoplight. The increased anxiety of the first driver may be captured by driver emotion data from one or more of the driver data sources 323 of the first vehicle. In one example, an anxiety classification model 310 of the first vehicle may assign a first anxiety classification to the first driver, based on the driver emotion data from the one or more of the driver data sources 323 of the first vehicle and a driver category of the first driver. The first anxiety classification may be transmitted to the second vehicle, including a location of the first vehicle, driver category of the first driver, and/or a road attribute code of the stoplight encountered (e.g., the cause of the anxiety of the first driver). Upon receiving the anxiety classification of the first driver, the second vehicle may use the anxiety classification of the first driver of the first vehicle to refine an anxiety classification of the second driver, or as an additional input into the rules based system 306 to determine whether or not to selectively inhibit the engine stop-start controller 304 of the second vehicle. In this way, a predicted anxiety level of the second driver, upon reaching a road attribute first encountered by the first driver, may be partially or totally based on an experienced anxiety level of the first driver at the road attribute.

The anxiety classification model 310 may receive the data from the plurality of devices, sensors, and systems of the vehicle 5 via a controller area network (CAN) 314. In an embodiment, the CAN may be a hardline vehicle connection (e.g., a bus) and may be implemented using any number of communication protocols generally known. Each anxiety classification model 310 may further take an output of the driver classification model 314 as input. In one example, the driver classification model 314 takes vehicle data and/or historical driver performance data received from a driver database 336 via the modem 330 of the CAN 314, and outputs a driver classification of the driver. The historical performance data may include, for example, a ratio of city/highway driving, average and standard deviation of a city speed, average and standard deviation of a highway speed, average and standard deviation of an accelerator pedal position, average trip length, standard deviation of distance, proximity of trip locations, brake score, among others. In other examples, no driver profile and/or historical driver performance data is received from the driver database 316 (e.g., for drivers with no previous driving history stored in the driver database 316), and the driver classification model 314 outputs a driver classification based on vehicle data (e.g., make, model, year, etc.) of the vehicle 5, and may refine the driver classification based on driver performance data received from one or more of the sensors 308 during operation of the vehicle 5.

Thus, the driver's future level of anxiety on the road segment may be predicted based on an anxiety classification of the driver assigned by a selected anxiety classification model 310, based on the driver category of the driver determined by the driver classification model 314. Each of the anxiety classification models 310 stored for a road segment category in the navigational database 315, for each driver category 310, may be developed as a composite model based on one or more outputs of individual emotion detection models based on audio, visual, and/or vital sign data of the driver, trained with data collected from a plurality of drivers on a plurality of road segments. Based on an output of the selected anxiety classification model 310 of the machine learning ensemble model 316 and/or one or more outputs of the one or more sensors 308, the rule-based system 306 may output a determination of whether to selectively disable or enable the engine stop-start controller 304. An example procedure for determining whether to selectively disable or enable the engine stop start controller 304 based on the output of the selected anxiety classification model 310 is described in greater detail below in reference to FIGS. 7-8, and an example procedure followed by the rule-based system 306 is described in greater detail below in relation to FIG. 9.

Figure 4:
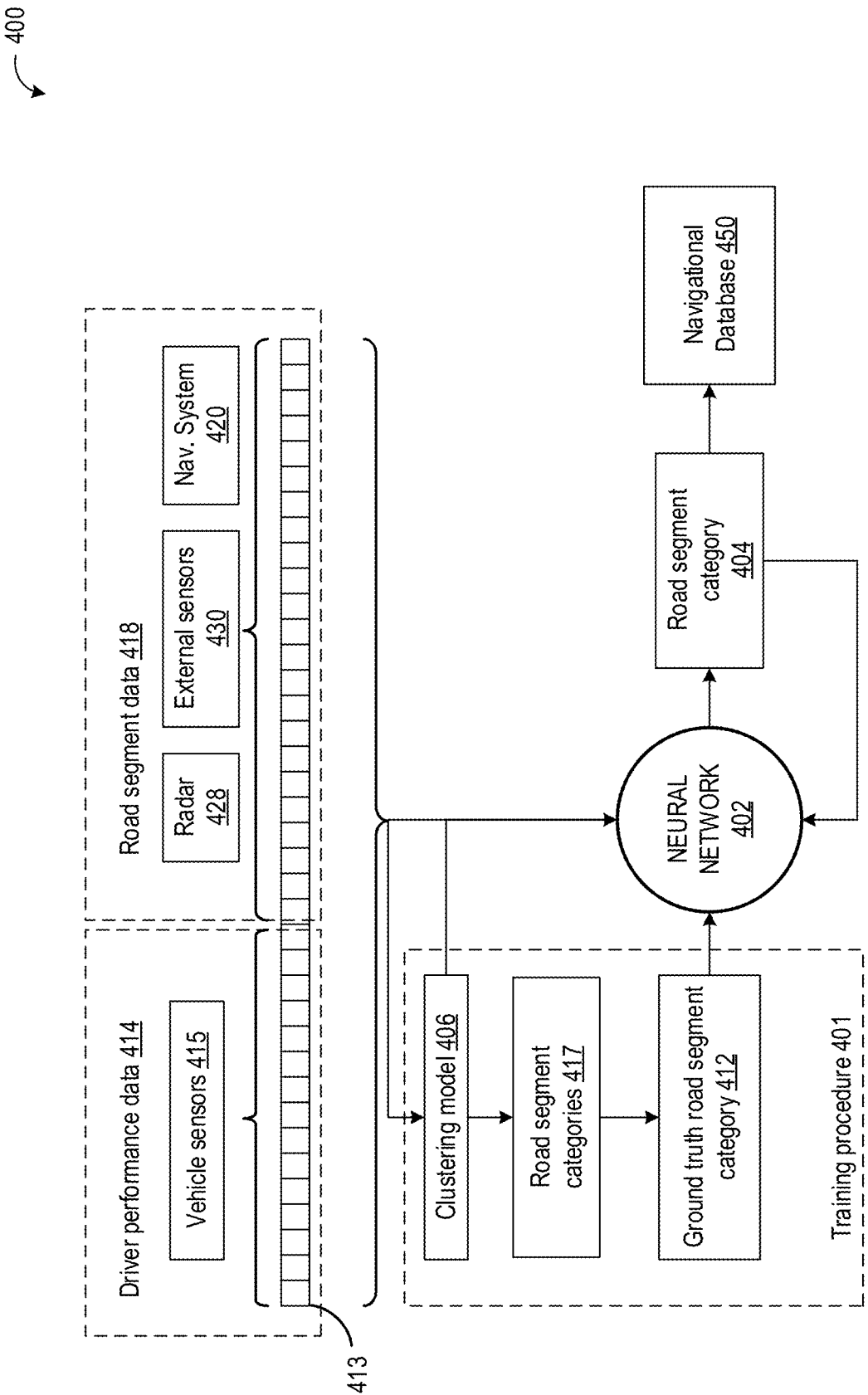
FIG. 4 shows a schematic depiction of a neural network system for classifying road segments.
Figure 5:
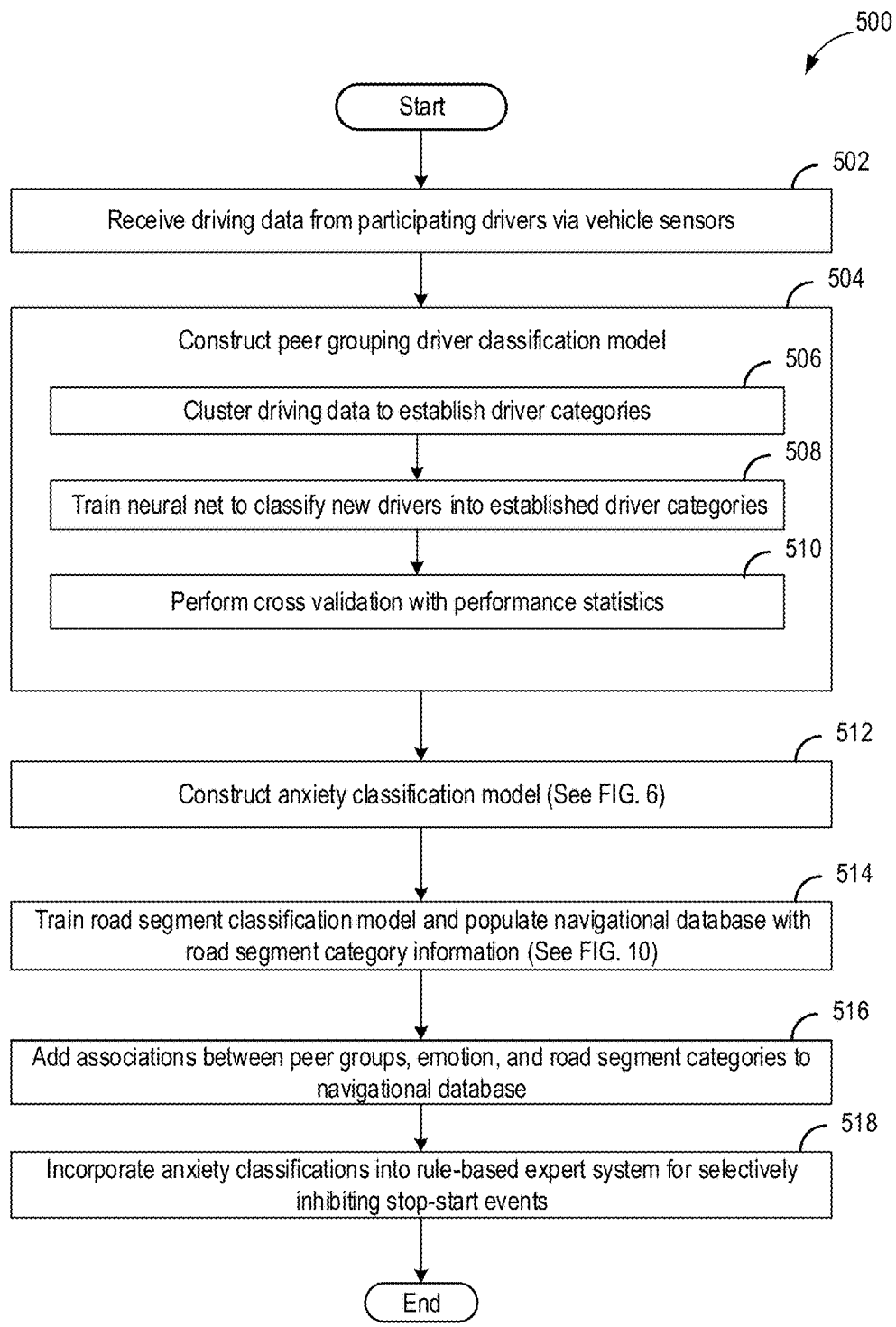
FIG. 5 shows a flow chart illustrating an example method for constructing a system to control an engine stop/start controller.

Turning now to FIG. 4, an example neural network training system 400 is shown, which may be used to train a neural network-based road segment classification model. Once trained, the neural network-based road segment classification model may classify a new road segment, as defined by one or more systems and/or sensors of a vehicle, into a road segment category (e.g., the road segment category 313 of engine stop-start control system 300 of FIG. 3A) based on one or more road attributes of the new road segment. The road segment category may further include driver emotion data for one or more driver categories, which may be used to adjust one or more settings of the vehicle (e.g., to selectively inhibit the engine stop-start controller 304 of FIG. 3A).

The neural network training system 400 may include a neural network 402, which may be trained to output a predicted road segment category 404 from a plurality of predictive data in the form of a vector 413 comprising a combination of driver performance data 414 and road segment data 418. The driver performance data 416 may include ongoing performance data received from one or more vehicle sensors 415 (e.g., the sensors 308 of the engine stop-start control system of FIG. 3A and/or the sensors 208 of the control system 202 of FIG. 2), including, for example, a % regeneration (SOC) realized or not realized, a starting SOC, and ending SOC, a depletion of SOC, an average speed, torque and/or braking of the vehicle, standard deviation of speed, torque and/or braking of the vehicle, etc.

In one example, the driver performance data 414 includes a plurality of numeric values, where each numeric value corresponds to an individual element of data of the driver performance data 414. In some examples, the values may include an output of a sensor (e.g., engine speed), while in other examples, the values may include a result of a calculation or processing of one or more outputs of a sensor (e.g., an average speed). In still other examples, the values may be a code generated based on one or more outputs of a sensor (e.g., a numeric value between 1 and 10 indicating a degree of aggression of the driver, level of experience, etc.).

The road segment data 418 may be supplied by one or more road data sources (e.g., the road data sources 325 of the engine stop-start control system 300 of FIG. 3A), including a navigational system 420, one or more external sensors 430 (e.g., cameras), and a radar 428. In one example, the road segment data 418 includes a plurality of numeric values, where the numeric values correspond to an encoding of road attributes identified at a location of the vehicle.

For example, the values of the vector 413 representing the road segment data 418 may include an average curvature of the road segment (e.g., where a low value may indicate a large degree of curvature and a high value may indicate a small degree of curvature, etc.); a presence of a stop light with a left turn option of road segment (e.g., where a value of 1.0 may indicate that a stop light is present in the road segment, and where a value of 0.0 may indicate that a stop light is not present in the road segment; and so forth). Other road attributes of the road segment data 418 may include average altitude, average elevation, intersections, yield situations, stop signs, four-way intersections, type of road (e.g., highway, residential, city, etc.), a road classification and/or road segment category, speed limit, change in speed limit, change in road curvature, road profile (e.g., banking, land 1+2 width, land 3+4 width, etc.), etc. The road attributes may be identified via the external sensors 430, navigational system 420, and/or radar 428. For example, one or more external cameras of the vehicle may detect a stoplight or a 4-way intersection, or a GPS onboard navigation system may identify a stoplight from an online navigational map hosted on a remote server. In one example, a new road segment is defined by the road segment data 418 in real time, and corresponds to an upcoming section of a route of the vehicle of a predetermined length (e.g., 100 yards, 0.25 miles, etc.).

During a training procedure 401 of the neural network 402, each road segment represented by a vector 413 is inputted into a clustering model 406, which may determine a plurality of different road segment categories 417 into which a training/test set of data (comprising a plurality of vectors 413) may be classified. The road segment categories 417 may be the same as or similar to the road segment categories 313, 354, and 356 of FIG. 3B. The neural network 402 is trained to generate a predicted road segment category 404 for each vector 413. The road segment category 404 outputted by the neural network 402 may be compared to a ground truth road segment category 412 generated by the clustering model 406. In one example, the ground truth road segment category 412 is a prototypical vector 413 that is determined to be a closest match to the vector 413. An error rate may be determined by a distance between the road segment category 404 and the ground truth road segment category 412. In one example, the difference is a squared Euclidean distance between the two vectors. The error rate may be back propagated through the layers of the neural network 402 in order to adjust a plurality of weights and biases of a plurality of nodes of the neural network 402, until the neural network 402 is able to classify the vectors 413 into the road segment categories 417 above a threshold accuracy (e.g., 95%).

Once the neural network 402 has been trained, the vectors 413 representing road segments and the road segment categories associated with the road segments by the trained network 402 may be stored in a navigational database 450, whereby additional data may be associated with road segment categories (e.g., anxiety classification models constructed from a plurality of drivers). In one example, a copy of the navigational database 450 is loaded into a memory of a vehicle controller (e.g., the memory 206 of controller 12 of FIG. 2), to be accessed by a machine learning ensemble model (e.g., the machine learning ensemble model 316 of FIG. 3A) when retrieving an anxiety classification for a road segment. The trained network 402 may take as input one or more new vectors 413 of new road data (e.g., as the driver operates the vehicle on a new road segment).

For example, as a vehicle proceeds along a route, it encounters various road attributes on its path (e.g., a curvature of the road, a banking of the road, a stoplight at an intersection, etc.). One or more of the external cameras 430 and the radar 428 may be used to detect the road attributes, and/or to identify additional road conditions (e.g., congestion, weather, etc.). Concurrently, sensors of the vehicle may output data that may be processed into driver performance data 414 (e.g., average speed of the vehicle, standard deviation of the speed of the vehicle, average and standard deviation of torque, etc.). The road attributes and/or conditions may be expressed as values in a vector 413 of the new road data (e.g., the road segment data 418), along with the driver performance data 414. The vector 413 of the new road data may be inputted into the trained neural network 402 to be classified to a road segment category 404. The road segment category 404 of the new road data, (e.g., based on the road attributes detected by the external sensors 430 and radar 428 of the vehicle) may be outputted to a controller of the vehicle to adjust one or more settings of the vehicle in anticipation of the upcoming road attributes.

Further, additional information may be associated with the road segment categories for additional customization of one or more settings of the vehicle. In one example, emotional data collected from a plurality of drivers may be processed and aggregated to create one or more anxiety classification models (the anxiety classification models 310 of FIGS. 3A and 3B) for each of the road segment categories stored in the navigational database 450. The anxiety classification models may be used to associate one or more anxiety levels with new road segments detected by the vehicle during operation, where each of the one or more anxiety levels corresponds to a driver category.

In one example, a road segment category segment 404 retrieved from the navigational database 450 may be an input into a rule-based system (e.g., the rule-based system 306 of the engine stop-start control system 300 of FIG. 3A), which may output a determination of whether to selectively enable or disable a stop start controller during operation on the road segment, such as the engine stop-start controller 304 of FIG. 3A. The determination of the rule-based system to selectively inhibit the engine stop start controller is described in greater detail below in relation to FIG. 9.

Referring now to FIG. 5, an exemplary method 500 shows a high-level procedure for determining whether to selectively inhibit an engine stop-start controller of a vehicle, such as the engine stop-start controller 304 of the engine stop-start control system 300 of FIG. 3A. Instructions for carrying out method 500 and the rest of the methods included herein may be executed by a controller of the vehicle (e.g., the vehicle controller 302 of the engine stop-start control system 300 of FIG. 3A), and more specifically, by a processor of a controller of the vehicle, such as the processor 204 of the controller 12 of the control system 202 of FIG. 2, based on instructions stored on a memory of the controller, such as the memory 206 of the controller 12 of the control system 202 of FIG. 2, in conjunction with signals received from sensors of the engine system, such as the sensors described above with reference to FIGS. 2-4. Instructions for carrying out method 500 and the rest of the methods included herein may also be executed by a processor of a remote server (e.g., the cloud-based server 225 of FIG. 2).

As those of ordinary skill in the art will understand, the functions represented by the flow chart blocks may be performed by software and/or hardware. Depending upon the particular processing strategy, such as event-driven, interrupt-driven, etc., the various functions may be performed in an order or sequence other than illustrated in the figure. Similarly, one or more steps or functions may be repeatedly performed, although not explicitly illustrated. In one embodiment, the functions illustrated are primarily implemented by software, instructions, or code stored in a computer readable storage medium and executed by one or more microprocessor-based computers or controllers to control operation of the vehicle.

At 502, method 500 includes receiving driver data from a plurality of participating drivers operating a plurality of vehicles, via one or more sensors of each vehicle of the plurality of vehicles. The driver data may include data acquired from vehicle sensors such as engine sensors, pedal position sensors, wheel sensors, battery sensors, and so forth. For example, for each driver of the plurality of participating drivers, data may be collected from a pedal position sensor and processed (e.g., by the controller and/or by a remote server accessed by the vehicle) to determine acceleration data of the driver, or data may be collected via an engine throttle sensor and processed to determine average vehicle speeds, standard deviations of vehicle speeds, etc., of the driver. In one example, the driver data is used for constructing a peer grouping driver classification model, as discussed below at 504.

The driver data may also include data on an emotional state of the driver, including data acquired from a camera and/or microphone installed inside a cabin of the vehicle, one or more IOT devices worn by the driver, and/or an ECG device worn by the driver (e.g., the internal camera 320, internal microphone 318, the IOT devices 324, and the ECG device 322 of the engine stop-start control system 300 of FIG. 3A). For example, the driver data may include images of a facial expression of the driver recorded by the camera, a sound made by the driver recorded by the microphone, a pulse rate of the driver acquired by the IOT device, and/or a pattern of neural activation of the driver acquired by the ECG device. In one example, the data on the emotional state of the driver is used for constructing an anxiety classification model, as described below at 506.

Further, reference data may be associated with the driver data. For example, a set of GPS coordinates of a location of the vehicle may be associated with driver data collected at the location, whereby the driver data may be associated with a condition, characteristic, or feature of a road at the location. A time may be associated with the driver data collected at the time, whereby the driver data may be associated with a time-dependent condition of a road, such as congestion, lighting conditions, etc. In one example, the reference data is used for associating an emotional state of a driver with a segment of a road, as described below at 516.

A number of participating drivers may be large enough to support a minimum number (e.g., 3-4) of driver classifications (also referred to herein as driver categories) into which the plurality of participating drivers may be classified, where a distribution of the participating drivers corresponds to a naturally occurring driver distribution in the real world. In one example, the number of participating drivers is at least 1000 drivers.

In some examples, each of the vehicles of the plurality of vehicles may be of the same make and model (e.g., the vehicle 5 of FIG. 1). In other examples, the vehicles of the plurality of vehicles may be of different makes and models, where each of the different makes and models includes an engine stop-start control system (e.g., the engine stop-start control system 300 of FIG. 3A) and a modem, and whereby controllers of the vehicles may communicate wirelessly with controllers of other vehicles and/or a cloud-based server or network.

The participating drivers may operate the vehicles in a selected area. In some examples, a size of the selected area may be limited (e.g., to a zip code, a city, a county, etc.), for example, to maximize a concentration of vehicles participating in a V2V network. In other examples, the size of the selected area may be unlimited, with drivers participating from different zip codes, cities, counties, regions, states, etc., for example, to maximize a number of participating drivers. In still other examples, the selected area may be the entire world, where data is aggregated from drivers worldwide.

The selected area may include a broad range of characteristics and features, whereby the drivers are exposed to varied driving conditions that elicit varied levels of anxiety. For example, the range of different characteristics and features may include sections that are straight or curved, on single lane roads, multi-lane roads, highways, and/or bridges, with portions of different slopes including hills and flat areas. The range of different characteristics and features may include diverse traffic features, such as stop signs, left-hand and right-hand turns, 4-way intersections, stoplights, etc. Further, the selected area may include a plurality of different road conditions, for example, urban roads, rural roads, unpaved roads, etc. Further still, the route may include a plurality of different traffic conditions, for example, areas of high congestion, areas of moderate congestion, and/or areas of low congestion.

At 504, method 500 includes constructing the peer grouping driver classification model from the driver data, which assigns a driver classification to each driver of the participating drivers. In one example, the driver classifications correspond to a plurality of peer groupings, where each peer grouping represents a category of drivers who share similar characteristics, and each driver is classified to a peer grouping. For example, one peer grouping may comprise drivers characterized as aggressive or impatient, while a different peer grouping may comprise drivers characterized as timid or lacking confidence, based on the driver data. In one example, the peer groupings may be based on factors such as vehicle type or age, driving behaviors (e.g., average speed and/or acceleration, etc.), or an experience level of the driver (e.g., a length of a driving history), or a driving style (e.g., cautious, smooth, abrupt, etc.) of the driver, or a driving pattern of the driver (e.g., a commuter, a travelling salesman on a route, etc.). Further, the peer groupings may be based on a combination of these and/or other factors.

In one example, the peer groupings may include a first peer level and a second peer level, where in the first peer level drivers are classified based on vehicle data, and in the second peer level drivers are classified based on driver data. For example, a driver may be assigned a driver classification based on the first peer level data when the driver starts to participate, and no historical data is available. The first peer level may consider vehicle data such as a make and model of the vehicle, a powertrain of the vehicle, a year of the vehicle, and so forth. The driver may be assigned a driver classification based on the second peer level data when enough data is collected to support a characterization of the second peer level. For example, the participating drivers may be categorized based on driving characteristics (e.g., how, where, and/or when a driver drives the vehicle). In some examples, the driving characteristics include one or more patterns of driving, such as whether a driver is a commuter, whether the driver travels on regular routes or irregular routes, and so forth. In some examples, the driving characteristics include a frequency of driving, such as a degree of regularity of the driver operating the vehicle. In some examples, the driving characteristics include a driving environment, for example, whether the driver operates the vehicle in a rural or urban environment, and/or whether the driver drives in an area of high or low congestion. Driving characteristics may also include a time of driving (e.g., during peak hours, in the evenings, etc.). It should be appreciated that the examples provided herein are for illustrative purposes, and the driver classifications may be assigned based on other driving, vehicle, or other characteristics, or a combination of different characteristics, without departing from the scope of this disclosure.

For example, as a driver operates the vehicle, the controller of the vehicle may transmit driver data that reflects the driving characteristics of the driver from the vehicle to a remote server in a cloud. The driver data may be saved in a database, and used to construct a profile of the driver and refine the profile over time. The driver data may specifically include, for example, statistical information such as average speeds in different circumstances or in different environments, as well as standard deviations, route data, proximity of destinations, driving duration data, braking habits, etc. Further, the driver data may include information about the driver's use of different modes or systems of the vehicle, such as regenerative breaking, cruise control, fuel efficiency mode, etc. In some examples, the driver data may be aggregated across a plurality of participating drivers, for example, to determine the peer groupings used by the peer grouping driver classification model.

Constructing the peer grouping driver classification model includes, at 506, clustering the driver data to establish a plurality of driver categories (e.g., peer groupings). In some examples, clustering the driver data includes clustering the first peer level data via a first clustering process, and clustering the second peer level data via a second clustering process. In one example, one or more machine learning clustering algorithms executed by a processor of a server in a cloud (e.g., the cloud based server 225 of FIG. 2) may be used to determine one or more natural clusters of the first peer level data in the first clustering process and one or more natural clusters of the second peer level data in the second clustering process. In this way, the participating drivers may be assigned classifications based on similar driving or vehicle characteristics.

In one example, a K-means clustering algorithm is used, where the input is a set of vectors, each vector comprising the driver data of one driver of the participating drivers (e.g., the first peel level driver data in the case of the first clustering process, and the second peer level data in the case of the second clustering process). The output of the K-means clustering algorithm is a driver classification into one of n possible classes, where n is the number of peer groupings (e.g., driver categories), and where each class is represented by a prototypical vector. As the machine learning/AI routine executes, one or more values of each of the prototypical vectors are iteratively adjusted to minimize a sum of squared Euclidean distances between the input vectors and the target vectors, to determine an optimal set of prototypical vectors for classifying the drivers into n categories. Further, a number of the prototypical vectors may be iteratively adjusted to determine an optimal number of driver categories n.

For example, the first peer level data may include a make, model, and year of a vehicle. The first clustering process may determine an optimal number of natural clusters (e.g., driver categories) n into which the participating drivers may be optimally grouped, where each driver of the participating drivers is classified into a driver category of the n driver categories based on a similarity to a make, model, and year of a prototypical vehicle of the driver category.

The second peer level data may include, for example, a ratio of city/highway driving, average and standard deviations of city speed, highway speed, accelerator pedal position, and trip length, a proximity of trip locations, a brake score, and/or percentages of driving time with electric vehicle (EV) on/off, eAssist, regenerative braking, eLaunch, time coasting, time coasting with brakes, time creeping (e.g., driving 5 miles per hour or less), and so forth. The second clustering process may determine an optimal number n of natural clusters (e.g., driver categories) into which the participating drivers may be optimally grouped, where each driver of the participating drivers is classified into a driver category of the n driver categories based on a similarity of the second peer level data of the driver to the second peer level data of a prototypical driver of the driver category (e.g., a proximity of the second peer level data vector of the driver to the prototypical second peer level data vector).

Constructing the peer grouping driver classification model includes, at 508, training a neural network to classify new drivers into established driver categories (e.g., classifications). For example, once the driver classifications have been established via the one or more clustering algorithms, training and test datasets may be compiled by pairing the vectors of the participating drivers (input vectors) with the corresponding prototypical vectors of the driver categories into which the drivers have been classified (target vectors). The training and test datasets may be used to train the neural network, and once the neural network is trained, a new driver vector formed from the first or second peer level data of a new driver may be inputted into the neural network, and the neural network may output a prototypical vector most similar to the new driver vector. The prototypical vector may indicate a classification of the new driver into one of the established driver categories (e.g., the category defined by the prototypical vector). The neural network may be trained to output a category of the driver, for example, based on a distance between the vector formed from the first or second peer level data of the new driver and one or more prototypical vectors of the categories, where the category assigned to the new driver corresponds to the prototypical vector with the smallest distance from the new driver vector.

Constructing the peer grouping driver classification model includes, at 510, performing cross validation with performance statistics to validate and/or refine the driver classification model. For example, for each new driver classified to a driver category by the neural network, a statistical analysis may be performed on the driver data of the new driver to validate the classification of the new driver to the driver category. As a result of the cross validations performed on new participating drivers at 510, the driver classification model may be refined and/or a new driver classification may be adjusted.

At 512, method 500 includes constructing an anxiety classification model, which may assign an anxiety classification to a driver based on data acquired from one or more internal sensors of the vehicle. For example, when operating the vehicle on a stressful or anxiety-inducing road segment, a facial expression of the driver may indicate an anxiety level of the driver, which may be captured by a dashboard camera. Similarly, the driver may make a verbal expression or a sound indicating the anxiety level of the driver (e.g., a gasp, exclamation, etc.). A Bluetooth® enabled device that monitors one or more vital signs of the driver, such as a fitness tracker or smart watch, may capture a change in a pulse of the driver or a brain-computer interface (BCI) device such as an Emotiv® device may capture a pattern of neural activity of the driver, indicating an anxiety level of the driver. Based on a combination of anxiety-related driver data of the driver, the level of anxiety of the driver may be estimated for the road segment by the anxiety classification model. Further, the anxiety levels of drivers within each of the driver categories may be aggregated (e.g., averaged) to generate an anxiety level for each of the driver categories for the road segment, which may be associated with the road segment in a navigational database, as described above in relation to FIG. 4. Construction of the anxiety classification model is described in further detail in reference to FIG. 6.

At 514, method 500 includes training a road segment classification model and populating a navigational database (e.g., the navigational database 450 of neural network training system 400 of FIG. 4) with road segment category information. For example, as each vehicle driven by the plurality of participating drivers drives along a route, the route may be divided into a plurality of road segments of a predetermined length (e.g., 100 yards). Each road segment may include one or more road attributes detected by sensors of the vehicle (e.g., the road data sources 325 of FIG. 3A) while operating on the road segment. The road segments collected by the plurality of vehicles may be categorized by a clustering algorithm, and a neural network (e.g., the neural network 402 of the neural network training system 400 of FIG. 4) may be trained to classify the road segments to a road segment category based on the one or more road attributes. Once the neural network is trained, a copy of the trained neural network may be used by each vehicle of the plurality of vehicles to classify new road segments to a road category. Further, the road segment—road segment category pairs may be stored in the navigational database along with additional data (e.g., emotional data), such that the additional data may be retrieved based on the road segment category. The training of the road segment classification model and populating of the navigational database is described in greater detail below in relation to FIG. 10.

At 516, method 500 includes making the associations between peer groups, emotion, and road segment categories, whereby the road segment categories of the navigational database are assigned one or more anxiety classification models based on an estimated (e.g., average) level of anxiety experienced by drivers. The one or more anxiety classification models correspond an equal number of peer groupings (e.g., driver categories), whereby for each road segment category of the navigational database, a level of anxiety may be predicted for each driver category by an anxiety classification model corresponding to each driver category. Thus, for an upcoming road segment, when road segment category information is retrieved from the navigational database, the controller may determine an anxiety classification associated with the driver category of the driver for the upcoming road segment. In one example, the anxiety classification is used by the controller to determine whether to selectively inhibit an engine stop-start controller of the vehicle.

For example, in an urban area, a first road segment may comprise a straight section of road, whereby the average level of anxiety generally produced while driving on the first road segment may be low. A second road segment may include a 4-way stop with multiple yield scenarios, whereby the average level of anxiety generally produced while driving on the second road segment may be moderate. A third road segment may include a congested stoplight without turn arrows, whereby the average level of anxiety generally produced while driving on the third road segment may be high (e.g., due to having to monitor a plurality of behaviors of other drivers).

A first driver may be categorized in a first peer grouping (e.g., by the driver classification model), corresponding to drivers of moderate experience operating in urban environments. A second driver may be categorized in a second peer grouping, corresponding to drivers of moderate experience operating in rural environments.

For the first driver, who is accustomed to urban environments, the first road segment may produce low anxiety, the second road segment may produce moderate anxiety, and the third road segment may produce high anxiety. However, for the second driver, who is not accustomed to urban environments, the first road segment may produce moderate anxiety, and the second road segment and third road segment may produce high anxiety. Therefore, a first predicted anxiety level may be associated with the first peer grouping (e.g., the category of the first driver) by a first anxiety classification model in the navigational database, and a second predicted anxiety level may be associated with the second peer grouping (e.g., the category of the second driver) by a second anxiety classification model in the navigational database, for each of the first segment, the second segment, and the third segment. In this way, for a road segment of a route of a vehicle, a predicted anxiety level can be retrieved from the navigational database for a driver category that corresponds to a driver of the vehicle.

In one example, the predicted anxiety level of the driver, based on the driver category of the driver, is used to selectively inhibit a stop-start controller of an engine of the vehicle. For example, when a driver stops the vehicle at a four-way intersection where the driver intends to make a left turn, the driver may experience an increased level of anxiety, for example, due to a stress associated with determining when to initiate the left turn. If the stop-start controller is enabled, the stop-start controller may turn off the engine to increase a fuel efficiency of the vehicle. The stopping of the engine may further increase the level of anxiety of the driver, due to a fear that the engine might not start upon initiation of the left turn. To prevent or reduce such anxiety, a controller of the vehicle may retrieve upcoming road segment information from one or more sensors of the vehicle, determine a driver category of the driver from a driver classification model (e.g., the driver classification model 314 of FIG. 3A), determine a road segment category of the upcoming road segment using a road segment classification model, and look up an anxiety classification of a resulting road segment category of the upcoming road segment corresponding to the driver category. If the anxiety classification indicates a potential high level of anxiety of the driver on the road segment, the controller may selectively inhibit the stop-start controller, whereby the engine will not turn off when the vehicle stops at the four-way intersection. As a result, the anxiety level of the driver may not be increased.

At 518, method 500 includes incorporating anxiety classifications into a rule-based expert system for selectively inhibiting stop-start events. The rule-based expert system considers the anxiety classification of the road segment along with one or more other factors. For example, using the stop-start controller may rely on a battery state of charge (SOC) being sufficient to power one or more systems of the vehicle with an engine off. If the battery SOC is below a threshold charge (e.g., 10%, the rule-based system may disable the stop-start controller, whereby the engine may not be turned off during engine idle conditions. An exemplary embodiment of a rule-based system is described in greater detail below in relation to FIG. 9.

In this way, a method is provided for an anxiety detection-based adaptive stop-start inhibitor that relies on aggregating data over a plurality of drivers, leveraging collective information, and borrowing from a connected vehicle platform to classify driver behaviors and support the development and refining of the road segment, driver, and anxiety classification models used by the adaptive stop-start inhibitor. Based on one or more outputs of the road segment, driver, and anxiety classification models, driver anxiety may be reduced by selectively inhibiting the stop-start controller prior to reaching high-anxiety scenarios caused by road attributes such as four-way intersections, stop lights, hills, and so on. Further, robust anxiety assessments may be generated by relying on a combination of facial expression information, audio information, vital sign information, and changes in electrical activity of the brain.

Figure 6:
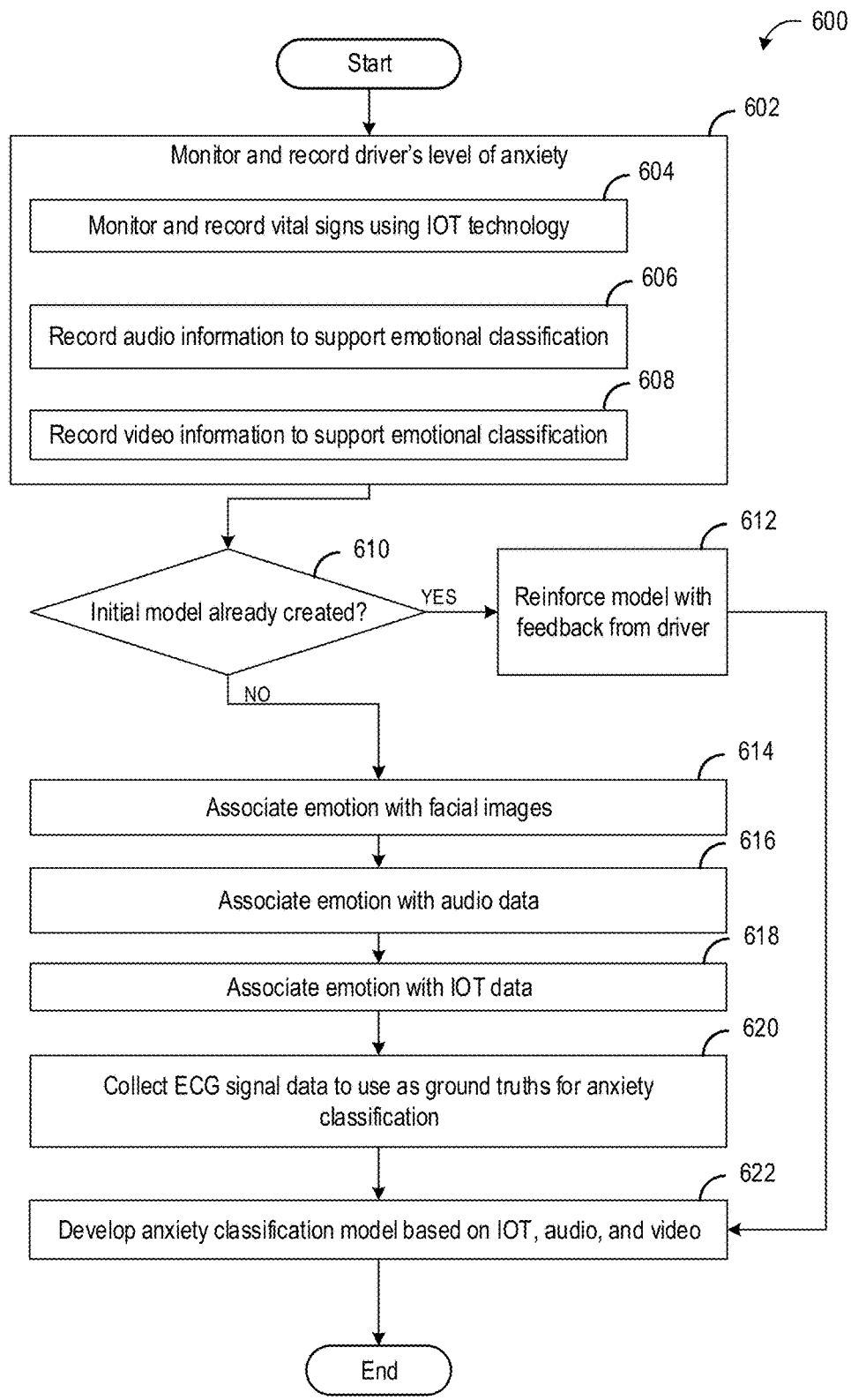
FIG. 6 shows a flow chart illustrating an example method for constructing an anxiety classification model.

Referring now to FIG. 6, an exemplary method 600 is shown for constructing one or more anxiety classification models, which may be used to assign a level of anxiety to a driver and/or a category of the driver on a road segment based on data acquired by one or more internal sensors of a vehicle driven by the driver. The anxiety classification model may be the same as or similar to the anxiety classification model 310 of engine stop-start control system 300 of FIG. 3A. In one example, the driver is assigned a level of anxiety based on a peer grouping of the driver, where each peer grouping has a different anxiety classification model. For example, a driver of a peer grouping corresponding to novice drivers may have an anxiety classification model that detects a high anxiety level of the driver based on a visible facial expression of alarm of the driver, while a driver of a peer grouping corresponding to expert drivers may have an anxiety classification model that detects a high anxiety level of the driver based on a subtle facial expression of concern of the driver.

At 602, method 600 includes monitoring and recording the driver's level of anxiety while the driver is operating the vehicle, via sensors of the vehicle. At 604, monitoring and recording the driver's level of anxiety includes monitoring and recording one or more vital signs of the driver using IOT technology. For example, a Bluetooth®-enabled device such as a fitness tracker or a smart watch worn by the driver that is capable of monitoring elevated vital signs may register a change in a pulse of the driver. The change in the pulse of the driver may be transmitted to a controller of the vehicle via Bluetooth®, where the change in the pulse of the driver may be transmitted to a remote server (e.g., the cloud-based server 225 of FIG. 2), where the change in the pulse of the driver may be incorporated into the anxiety classification model. For example, an increase in the pulse of the driver may indicate an increased anxiety of the driver, while a decrease in the pulse of the driver may indicate a decreased anxiety of the driver.

At 606, monitoring and recording the driver's level of anxiety includes recording audio information to support emotional classification. In one example, an audio recording of a driver may be captured by an internal microphone of the vehicle, such as the internal microphone 318 of engine stop-start control system 300 of FIG. 3A. In one example, an internal microphone is installed in the dashboard of the vehicle. In other examples, the internal microphone is installed elsewhere in a cabin of the vehicle (e.g., a ceiling, a door, etc.). When the driver experiences an increased level of anxiety as a result of a driving condition (e.g., a busy stop light, a congested area, a four-way intersection on a hill, etc.), the driver may make a sound, such as an exclamation, or an audible breathing pattern of the driver may be disrupted. As one example, the driver may gasp, or hold their breath, or change a rate of breathing. The sound may be voluntary, or the sound may be involuntary. Further, the driver may make one or more verbal statements that express or suggest an increased level of anxiety. For example, the driver may communicate a level of anxiety or frustration to a passenger of the vehicle, or to themselves. As another example, the driver may speak to a passenger of the vehicle in a manner that communicates an unspoken level of anxiety or frustration. The sounds, statements, expressions, breathing, and/or other audio data of the driver may be recorded by the microphone and transmitted by the controller to the remote server, where the audio data of the driver may be incorporated into the anxiety classification model.

For example, a driver may stop at a stoplight in heavy traffic, in preparation for a left turn. When the stoplight turns green, the driver may begin to monitor a plurality of vehicles proceeding through the green stoplight in the opposite direction. Each vehicle of the plurality of vehicles may be operating at a different speed, and a distance between each vehicle of the plurality of vehicles may vary, where executing the left turn may involve identifying a viable "window" between two vehicles of the plurality of vehicles. Monitoring the traffic to identify a viable window may generate an increased level of anxiety of the driver, and as a result of the increased level of anxiety, the driver may make an exclamation, which may be detected by a dashboard microphone. The controller may create and process an audio clip of the exclamation, which may be transmitted to the remote server to be incorporated into the anxiety classification model.

At 608, monitoring and recording the driver's level of anxiety includes recording video information to support emotional classification. In one example, a video recording of a driver may be captured by an internal camera of the vehicle, such as the internal camera 320 of engine stop-start control system 300 of FIG. 3A. In one example, an internal camera is installed in the dashboard of the vehicle. In other examples, the internal camera is installed elsewhere in a cabin of the vehicle (e.g., a ceiling, a door, etc.). In one example, the video data includes one or more static images acquired by the internal camera. In other examples, the video data includes a video recording with multiple frames acquired by the internal camera.

When the driver experiences an increased level of anxiety as a result of a driving condition, as in the example of the congested stoplight described above at 606, a facial expression of the driver may change. For example, a brow of the driver may become furrowed, lips of the driver may be pursed, etc. Additionally, a position of a face of the driver may change, for example, from facing a windshield of the vehicle to facing out of a door window of the vehicle. The change of facial expression, change of position of the face of the driver, and/or other video data of the driver may be recorded by the internal camera and transmitted by the controller to the remote server to be incorporated into the anxiety classification model. Further, photoplethysmography may be used to detect changes in a pulsatile volume of blood in the face of the driver from images taken by the internal camera. For example, images taken over a period of time may be used to monitor a heart rate of the driver. If the heart rate of the driver increases, it may be inferred that the driver is experiencing an increased rate of anxiety.

The IOT, audio, and video data recorded at a moment in time may be processed collectively to develop a more robust anxiety classification model than would be possible using the IOT, audio, and video data separately. For example, as a driver navigates a multiple-yield 4-way intersection, a camera of the vehicle may capture one or more images of a facial expression of the driver, which may indicate a level of anxiety-producing confusion regarding a turn-taking priority. An internal microphone of the vehicle may capture one or more sounds made by the driver, such as a disrupted breathing pattern or one or more exclamations. A fitness tracker worn by the driver may capture an increase in a pulse of the driver, indicating an increased anxiety of the driver. Some drivers may show an increased anxiety in a facial expression, but not in an audible way, while other drivers may show increased anxiety in a change of pulse, but not in a facial expression. As an anxiety level of each driver may be exhibited in a different manner, by combining anxiety data collected from visual, audible, and physiological modes, an accuracy of the anxiety classification model may be increased.

Processing one or more images acquired via the internal camera to detect an emotional state of the driver may rely on one or more systems for detecting a face and/or changes in the face of the driver. Referring briefly to FIG. 11, a facial detection system used in a vehicle is shown where the face of the driver is captured via a dashboard video camera, according to an exemplary embodiment. An internal cabin view 1102 shows a driver operating a vehicle, while a dashboard camera 1104 captures the face of the driver. The face of the driver is depicted in images 1106, 1108, and 1110, where one or more features of a facial expression of the driver are detected. For example, image 1106 shows a detection of facial features including a mouth, nose, and eyes of the driver, where a proportion, positioning, and/or other aspects of the detected facial features are represented. Image 1108 shows a detection of the driver's eye in an image captured by the dashboard camera. Image 1110 shows a detection of the driver's eyelids. In one example, the detected features are used in identifying an emotion of the driver (e.g., anxiety), for incorporation into the anxiety classification model (e.g., the facial emotion detection model 380 of anxiety classification model 310 of FIG. 3B).

Returning to FIG. 6, at 610, method 600 includes determining whether an initial anxiety classification model has been created. If an initial anxiety classification model has been created at 610, method 600 proceeds to 612, where method 600 includes reinforcing the anxiety classification model with the IOT, audio, and video data collected from the driver. For example, if an anxiety classification generated by the anxiety classification model for a road segment does not match the emotional classification of the driver generated by the IOT, audio, and video data collected from the driver on the road segment, the anxiety classification model may be adjusted to generate a new anxiety classification, where the new anxiety classification more closely matches the emotional classification of the driver generated by the IOT, audio, and video data. Further, in some examples, the driver may provide verbal feedback that may be used to refine the anxiety classification model. Alternatively, if an initial anxiety classification model has not been created at 610, method 600 proceeds to 614.

At 614, method 600 includes associating emotion with facial images. For example, a facial expression of the driver recorded by a dashboard camera may be associated an emotion based on one or more facial emotion detection models based on one or more algorithms and/or techniques (e.g., application of Viola-Jones face detection, facial extraction algorithms, principal component analysis (PCA), Fischer linear discriminant analysis (LDA), histogram of oriented gradients (HOG) feature extraction, multi-class support vector machines (SVM), etc.). At 614, method 600 associates an emotion with audio data. In one example, associating an emotion with audio data may include referencing an established collection of emotional speech from a database. For example, a database may include a plurality of emotional utterances, where each emotional utterance of the plurality of emotional utterances is associated with an emotion and/or a degree of emotion. A sound uttered by the driver may be inputted into the database, which may output a predicted emotion corresponding to the utterance of the driver. In other examples, a different procedure may be used, whereby driver samples are split into positive (happy, calm, etc.) and negative (angry, fearful, sad, etc.) categories based on video/audio/IOT analysis. For example, some audio samples of the driver may be characterized as positive, where the driver may not be experiencing an increased anxiety, and other audio samples of the driver may be characterized as negative, where the driver may be experiencing an increased anxiety. By examining the audio samples in conjunction with other emotion data collected concurrently, driver utterances may be classified as either indicative of an increased anxiety of the driver, or not indicative of an increased anxiety of the driver. Further, in some examples a convolutional neural network may be applied to classify audio samples to an emotion, for example, using ECG data from a device worn by the driver for validation. It should be appreciated that the examples provided herein are for illustrative purposes, and other techniques for detecting emotion from a facial expression or an audio sample may be used without departing from the scope of this disclosure.

At 616, method 600 includes associating emotion with IOT data. In one example, the IOT data includes numeric values, such as heart rate (e.g., pulse), galvanic skin response, etc. Threshold values may be used to determine a level of anxiety of the driver. For example, a smart watch worn by the driver may register a heart rate of the driver at rest. When operating the vehicle in a stressful situation (e.g., at an intersection, stoplight, high traffic, etc.) the heart rate of the driver may increase. If the increase of the heart rate of the driver is above a threshold increase (e.g., 10%), an anxiety level associated with the driver may be increased. In one example, an anxiety level is indicated by a numeric value from 1 to 10, where 1 is a low level of anxiety. If the increase of the heart rate of the driver is above the threshold increase, the numeric value representing the level of anxiety of the driver may be incremented (e.g., from a 3 to a 5). Further, additional threshold increases may be used to determine a change in the anxiety level of the driver. For example, if a driver has an anxiety level represented by the number 3, and a first threshold increase is exceeded (e.g., 10%), the anxiety level of the driver may be incremented from 3 to 5. If a second threshold increase is exceeded (e.g., 20%), the anxiety level of the driver may be incremented from 3 to 6, and so on.

At 620, method 600 includes collecting ECG signal information to use as ground truths for anxiety classification. For example, a subset of the participating drivers may wear an ECG device (e.g., Emotiv®) configured to capture a neural pattern of the driver. The neural pattern may be compared with one or more known neural patterns identified with an emotion, whereby the driver may be assigned a known emotion corresponding to the neural pattern of the driver during operation. In some examples, the emotion of the driver may be confirmed (e.g., in advance, during calibration) with verbal feedback of the driver.

For example, a first neural activity pattern may be generated when the driver is anxious (e.g., as a result of a road condition or attribute), and a second neural activity pattern may be generated when the driver is not anxious. By comparing a neural activity pattern generated by the driver to a neural activity pattern known to be associated with an increased level of anxiety (e.g., because the level of anxiety of a wearer of the ECG device can be confirmed by the wearer), it may be determined whether the driver is experiencing an increased level of anxiety. Thus, as the IOT, audio, and video data is collected while the driver is operating the vehicle, the ECG data may be collected concurrently, whereby the IOT, audio, and video data capture indications of a same emotion registered by the ECG data. In this way, ground truth anxiety classifications may be generated for training or refining individual emotion detection models for associating emotion with facial images at 614, associating emotion with audio data at 616, and associating emotion with IOT data at 618.

At 622, method 600 includes developing an anxiety classification model based on the IOT, audio, and video models described above (e.g., the facial emotion detection model 380, audio emotion detection model 382, and physiological emotion detection model 384 of FIG. 3B). In one example, the anxiety classification model returns an average or weighted average of the outputs of the IOT, audio, and video models. In some examples, the weighted average is based on weights that are the same for all driver categories. In other examples, the weighted average is based on weights that are not the same for all driver categories. For example, it may be determined that for a first driver category, a facial detection model may produce a more accurate indication of a driver anxiety (e.g., as determined by comparing to ECG data) than an audio emotion detection model, while in a second driver category, an audio detection model may produce a more accurate indication of a driver anxiety than a facial emotion detection model, and so on. It should be appreciated that the examples provided herein are for illustrative purposes, and other methods for weighting different emotion detection models may be used without departing from the scope of this disclosure.

Driver feedback may also be used to develop and/or refine the anxiety classification model. One or more driving settings selected by the driver may indicate an increased or decreased anxiety, or propensity for anxiety of the driver. For example, a manual override of the engine stop-start system may be selected by the user via a manual override button on a dashboard of the vehicle. A manual override or a pattern of manual overrides of the engine stop-start system at a road segment may indicate an increased anxiety of the driver at the road segment, and therefore the anxiety classification model may be adjusted accordingly. In other examples, verbal driver feedback may be used, or another type of driver feedback.

Figure 7:
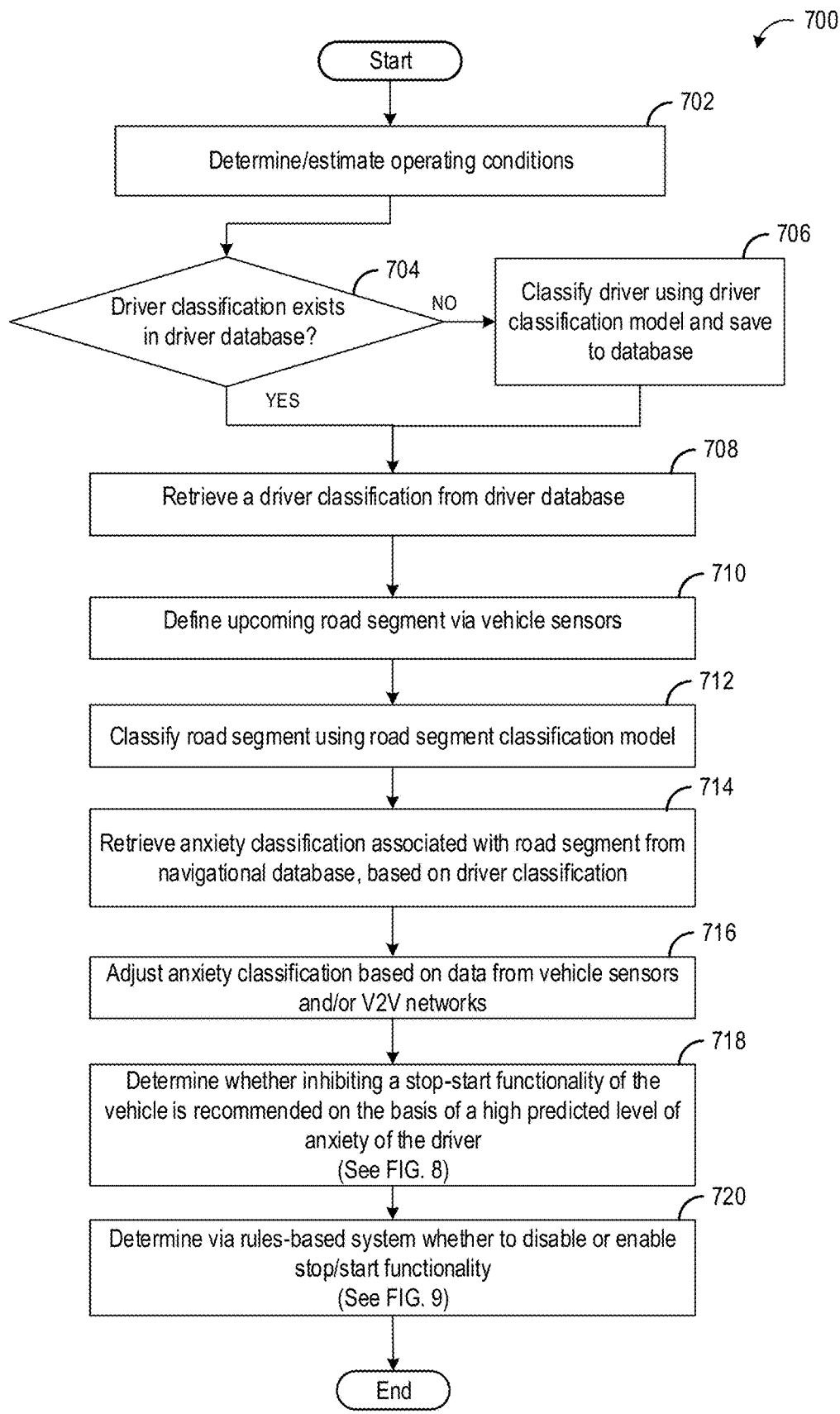
FIG. 7 shows a flow chart illustrating an example method for controlling an engine stop/start controller.

Referring now to FIG. 7, a method 700 is shown for controlling engine stop-start events of a vehicle according to one embodiment of this disclosure. Method 700 begins at 702 where method 700 includes determining and/or estimating operating conditions. For the purposes of this disclosure, determining and/or estimating operating conditions may occur when an engine of the vehicle is started and/or when operation of the vehicle is otherwise initiated. Operating conditions may include engine operating conditions such as engine speed, engine load, intake air flow rate and/or pressure, throttle position, accelerator pedal position, ambient pressure, ambient temperature, speed, exhaust temperature, and the like. The operating conditions may further include determining a state of charge of a battery, such as the battery 108 of vehicle 5 of FIG. 1.

At 704, method 700 includes determining whether a classification of a driver of the vehicle exists in a driver database (e.g., the driver database 336 of engine stop-start control system 300 of FIG. 3A). In some examples, the driver may have been previously classified to a driver category by a driver classification model (e.g., the driver classification model 314 of FIG. 3A) and the driver classification may be retrieved from the driver database. If at 704 it is determined that a classification of the driver does not exist in the driver database, method 700 proceeds to 706. At 706, method 700 includes classifying the driver using the driver classification model and saving the driver classification to the driver database. As described above in relation to FIG. 5, the driver classification model may assign a classification to the driver in accordance with a peer grouping of the driver, based on vehicle data of the driver and/or historical performance data of the driver. Alternatively, if at 704 it is determined that a classification of the driver exists in the driver database, method 700 proceeds to 708. At 708, method 700 includes retrieving a current classification of the driver from the driver database.

At 710, method 700 includes defining an upcoming road segment of a route of the vehicle based on vehicle sensor data. As the vehicle drives along a route, sensors of the vehicle may detect one or more road attributes as described above in relation to method 500 of FIG. 5. For example, a vehicle traveling along a route may detect, within a segment extending 100 yards ahead of the vehicle, a steep hill downward as a first road attribute, and a 4-way intersection at the bottom of the steep hill as a second road attribute. A controller of the vehicle may create a coded representation of the road segment, whereby the presence of the hill and the intersection are represented as numeric values in a vector, along with any other road attribute data (e.g., curvature, banking, etc.) At 712, method 700 includes classifying the road segment using a road segment classification model (e.g., the road segment classification model described in the neural network training system 400 of FIG. 4). In one example, the road segment classification model is a neural network that takes as input the vector representing the road segment described above, and outputs a road segment category of the road segment. At 714, method 700 includes retrieving an anxiety classification associated with the road segment from a navigational database (e.g., the navigational database 450 of FIG. 4), based on the driver classification retrieved at 708. As described above in method 500 of FIG. 5, the anxiety classification may indicate a level of anxiety of the driver when operating the vehicle on the road segment (e.g., due to one or more stress-inducing attributes of the road segment, such as an intersection, etc.). Further, each road segment in the navigational database may be associated with a plurality of anxiety classifications, where each anxiety classification of the plurality of anxiety classifications corresponds to a driver category. For example, for one category of drivers (e.g., experienced drivers), a low anxiety classification may be assigned to a road segment category, while for a different category of drivers (e.g., inexperienced drivers), a high anxiety classification may be assigned to a road segment category.

At 716, method 700 includes adjusting the anxiety classification retrieved from the navigational database for the road segment based on data from one or more sensors of the vehicle and/or V2V networks of the vehicle. For example, an external camera of the vehicle may detect snow on the road, and an external temperature sensor of the vehicle may measure a temperature that is below freezing. As a result, the vehicle controller may adjust the anxiety classification associated with the road segment to reflect an increased potential for driver anxiety. For example, if an anxiety classification of 6 is retrieved for the road segment from the navigational database, the anxiety classification of the road segment may be adjusted to 8 to reflect the increased potential for driver anxiety. Additionally, or alternatively, a first driver may be driving a first vehicle and a second driver may be driving a second vehicle along the route with the road segment described above, where the driver of the first vehicle and the driver of the second vehicle have the same driver category, the second vehicle is 100 yards behind the first vehicle, and there is no snow detected on the hill. In one example, the driver of the first vehicle may discover that the hill is unexpectedly slippery, and therefore the driver of the first vehicle may experience an increased anxiety. The increased anxiety of the driver of the first vehicle may be detected by an anxiety classification model of the first vehicle (e.g., via internal sensors of the first vehicle), and the increased anxiety of the driver of the first vehicle may be transmitted to the second vehicle via a V2V network. As a result of receiving the increased anxiety of the driver of the first vehicle, the controller of the second vehicle may adjust the anxiety classification of the road segment.

In another example, the first vehicle may begin to slide due to ice on the road segment, which may be detected by a sensor of the first vehicle (e.g., a wheel sensor). The driver of the first vehicle may not experience an increased anxiety as a result of the sliding, and thus anxiety data may not be transmitted to the second vehicle. However, the first vehicle may transmit to the second vehicle a warning that slippery conditions may be encountered ahead. As a result of receiving the warning that slippery conditions may be encountered ahead, the controller of the second vehicle may adjust the anxiety classification of the road segment. In still other examples, road, climate, and/or other driving condition data may be transmitted from an element of infrastructure located on the route of a vehicle via a vehicle-to-infrastructure (V2X) network.

At 718, method 700 includes determining whether inhibiting a stop-start functionality of the vehicle is recommended on the basis of a high predicted level of anxiety of the driver. An exemplary procedure for determining whether inhibiting a stop-start functionality of the vehicle is recommended on the basis of a high predicted level of anxiety of the driver is described in greater detail below in reference to FIG. 8.

At 720, method 700 includes determining, via a rule-based system, whether to disable or enable the stop-start functionality. An exemplary procedure followed by the rule-based system is described below in greater detail with reference to FIG. 9.

Figure 8:
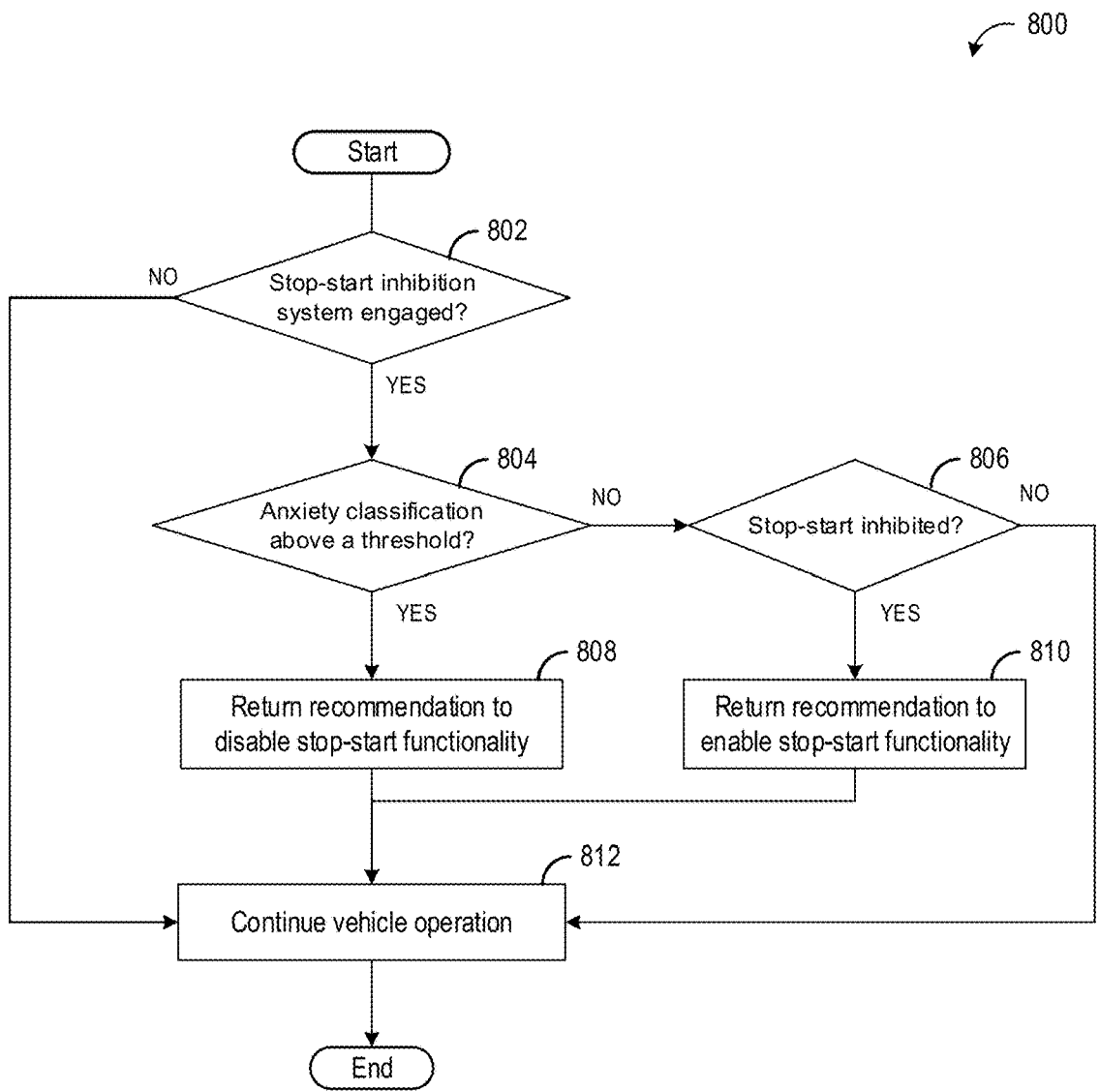
FIG. 8 shows a flow chart illustrating an example method for selectively inhibiting an engine stop/start controller.

Referring now to FIG. 8, an exemplary method 800 is shown for determining whether inhibiting a stop-start functionality of a vehicle is recommended on the basis of a predicted level of anxiety of a driver of the vehicle. Method 800 may be executed as part of the method 700 of FIG. 7. As described above, a predicted level of anxiety may correspond to an anxiety classification for a road segment on which the vehicle is operating, where a high anxiety classification may indicate a high predicted level of anxiety, and a low anxiety classification may indicate a low predicted level of anxiety.

Method 800 begins at 802, where method 800 includes determining whether a stop-start inhibition system is engaged. For example, stop-start inhibition may not be engaged because the driver has selected to manually override the stop-start control system, or because a battery SOC is below a threshold level (e.g., 10%), or for another reason. If the stop-start inhibition system is not engaged at 802, method 800 proceeds to 820, and operation of the vehicle continued. Alternatively, if the stop-start inhibition system is engaged at 802, method 800 proceeds to 804.

At 804, method 800 includes determining whether an anxiety classification of the road segment for a driver category of the driver is above a threshold anxiety classification. For example, the anxiety classification may be a number between 1 and 10, where 10 represents a high anxiety classification (e.g., indicating that the driver may experience a high predicted level of anxiety on the road segment), and where 1 represents a low anxiety classification (e.g., indicating that the driver may experience a low predicted level of anxiety on the road segment). In one example, the threshold anxiety classification is 5, representing an average or moderate anxiety classification. For example, if the anxiety classification of the road segment is 7 for the category of the driver, the anxiety classification is above the threshold, and if the anxiety classification of the road segment is 2 for the category of the driver, the anxiety classification is below the threshold.

If at 804 it is determined that the anxiety classification (e.g., the predicted level of anxiety) of the driver is above the threshold, method 800 proceeds to 808. At 808, method 800 includes returning a recommendation to disable stop-start functionality on a basis of a high predicted level of anxiety of the driver. In one example, the recommendation returned by method 800 at 808 is inputted into a rule-based system (e.g., the rule-based system 306 of the engine stop-start control system 300 of FIG. 3A), which may determine whether or not to disable or enable the stop-start functionality of the vehicle, as described in greater detail below in method 900 of FIG. 9.

Alternatively, if at 804 it is determined that the anxiety classification of the road segment for the driver is not above a threshold anxiety level, method 800 proceeds to 806. At 806, method 800 includes determining whether an engine stop-start functionality of the vehicle is in an inhibited state, for example, due to a high predicted anxiety level of the driver at a previous road segment. If at 806 it is determined that the stop-start functionality of the vehicle is not in an inhibited state, method 800 proceeds to 820, where operation of the vehicle is continued, and the stop-start functionality is not inhibited. Alternatively, if at 806 is determined that the engine stop-start functionality is in an inhibited state, method 800 proceeds to 810. At 810, method 800 includes returning a recommendation to enable the stop-start functionality, and method 800 proceeds to 812. At 812, method 800 includes continuing vehicle operation.

Figure 9:
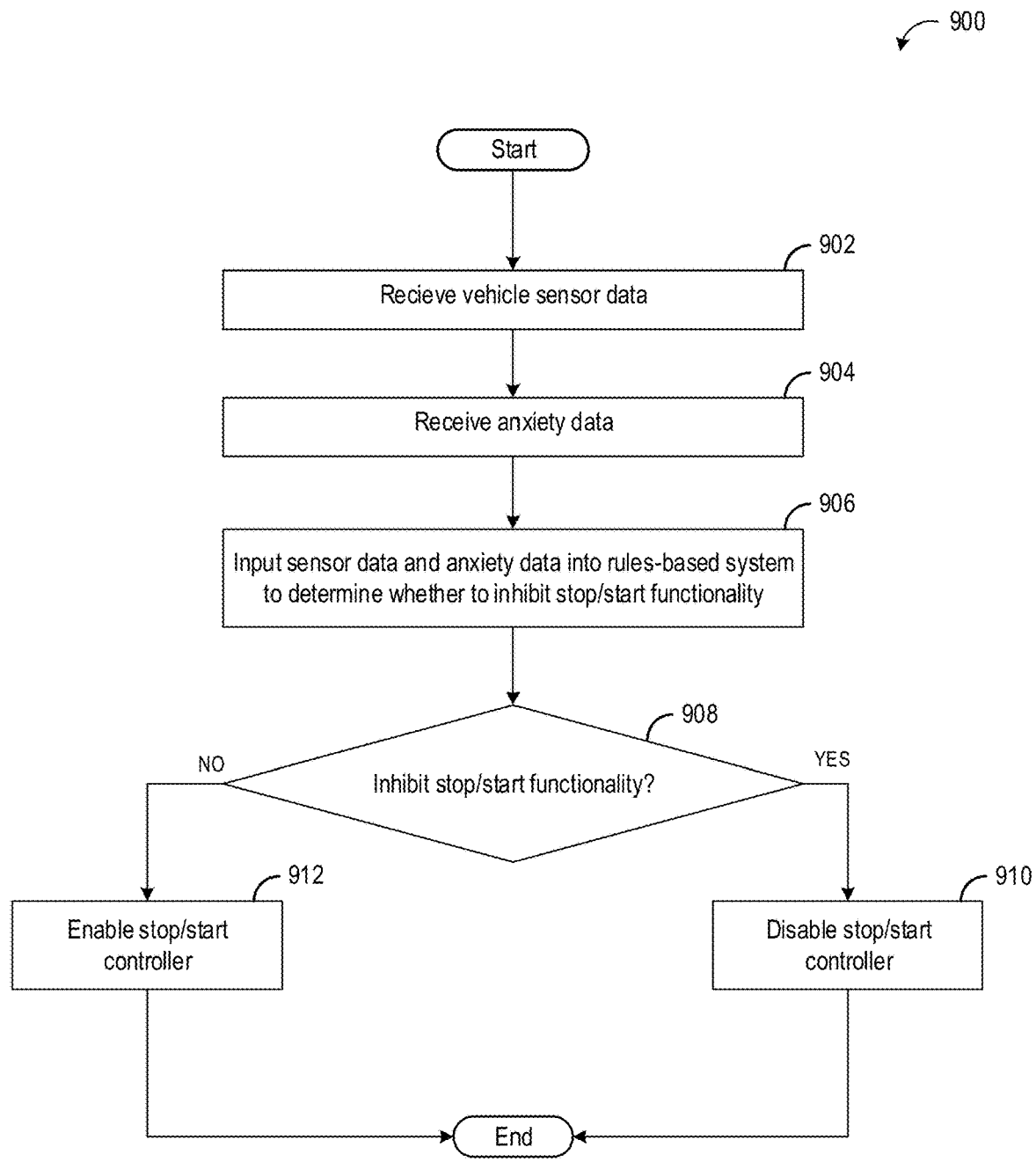
FIG. 9 shows a flow chart illustrating an example method for a rule-based system to determine whether to inhibit a stop-start controller.

Referring now to FIG. 9, an exemplary method 900 is shown for determining, via a rule-based system, whether or not to inhibit a stop-start controller of a vehicle such as the stop start controller 304 of engine stop-start control system 300 of FIG. 3A. The rule-based system may take as input a recommendation to inhibit a stop-start functionality of the vehicle generated by a procedure such as the procedure described in method 800 of FIG. 8, as well as one or more outputs of one or more vehicle sensors, such as the sensors 308 of engine stop-start control system 300 of FIG. 3A and/or the sensors 208 of control system 202 of FIG. 2. Method 900 may be executed as part of the method 700 of FIG. 7 described above.

At 902, method 900 includes receiving vehicle sensor data from the vehicle. For example, receiving vehicle sensor data may include receiving state of charge (SOC) data of a battery of the vehicle from a battery SOC sensor of the vehicle. The SOC data may indicate a capacity of the battery to maintain one or more systems of the vehicle without running an engine of the vehicle. If the SOC of the battery is below a threshold SOC (e.g., 10%), one or more powered systems of the car may not be maintained (e.g., internal and/or external lights of the vehicle, power brakes, climate control, etc.) and/or the battery may not have sufficient charge to power a restart of the engine after an idle stop. Therefore, the SOC of the battery may be considered by the rule-based system in determining whether to disable the stop-start control system.

Receiving vehicle sensor data may include detecting one or more driving settings of the vehicle. For example, the stop-start control system may include an option to manually override the start-stop control system (e.g., via a manual override button on a dashboard of the vehicle). If the driver frequently operates the vehicle in an environment that is stressful for the driver, the driver may experience an increased level of anxiety as a result of the operation of the stop-start controller, where the driver may worry that the engine might not turn on at a moment when the accelerator is adjusted by the driver. As a result of the increased level of anxiety, the driver may manually override the stop-start control system. If the vehicle sensor data indicates that the driver has manually overridden the stop-start control system, the rule-based system may disable the stop-start control system.

At 904, method 900 includes receiving anxiety data, in the form of an anxiety recommendation (e.g., a recommendation of whether to inhibit the start-stop controller based on a predicted anxiety level of the driver on an upcoming road segment). For example, the anxiety recommendation may be generated as described above in relation to method 800.

At 906, method 900 includes inputting the sensor data and the anxiety recommendation from method 800 into a rule-based system to output a result indicating whether to selectively disable or enable the stop-start functionality of the vehicle. In one example, the rule-based system considers the sensor data and the anxiety data sequentially in accordance with a pre-established hierarchy of conditions under which the stop-start controller is selectively inhibited, where the individual sensor data and the anxiety data may be ranked by a priority. For example, having a battery SOC above the threshold SOC may be a first criteria for disabling the stop-start functionality, where if it is determined from the sensor data that the battery SOC is not above the threshold SOC, the rule-based system may output a result to inhibit the stop-start functionality based on the battery SOC. If it is determined that the battery SOC is above the threshold SOC, the rule-based system may consider as a second criteria whether the driver has selected to manually override the stop-start functionality. If the driver has selected to manually override the stop-start functionality, the rule-based system may output a result to disable the stop-start functionality of the vehicle in accordance with the selection of the driver. If it is determined that the battery SOC is above the threshold SOC and that the driver has not selected to override the stop-start functionality, the rule-based system may consider the anxiety data of the driver, where if the anxiety data predicts a high level of anxiety of the driver on an upcoming road segment, the rule-based system may output a result to inhibit the stop-start functionality of the vehicle based on the predicted high level of anxiety of the driver. Alternatively, if the anxiety data predicts a low level of anxiety of the driver on the upcoming road segment, the rule-based system may not output a result to inhibit the stop-start functionality of the vehicle, and may consider other sensor data (e.g., engine condition data, pedal position data, etc.). In this way, the determination of whether to inhibit the stop-start functionality of the vehicle may be based on a decision chain, where individual sensor data and the anxiety data is considered in an order of importance and where the determination to inhibit the stop-start functionality is made upon one or more criterion of a plurality of criteria being met. It should be appreciated that the examples provided herein are for illustrative purposes, and that a different ordering or ranking of sensor and/or anxiety data may be used without departing from the scope of this disclosure.

At 908, method 900 includes determining, based on the output of the rule-based system, whether to inhibit the stop-start functionality. If it is determined at 908 that the stop-start functionality should be inhibited, method 900 proceeds to 910. At 910, method 900 includes disabling the stop-start controller. In one example, disabling the stop-start controller at 910 includes adjusting a state of the stop-start controller from an enabled state to a disabled state. In other examples, the stop-start controller may already be in the disabled state, and thus disabling the stop-start controller at 910 includes continuing the disabled state of the stop-start controller. For example, the vehicle may travel through a first road segment that includes a stressful road attribute (e.g., an intersection, a stoplight, etc.), followed by a second road segment that does not include any stressful road attributes. When approaching the first road segment, the stop-start controller may be inhibited in accordance with method 900 due to a predicted high level of anxiety of the driver. As a result, as the vehicle approaches the second road segment, the stop-start controller may be in a disabled state as result of inhibition on the first road segment.

Alternatively, if it is determined at 908 not to disable the stop-start functionality, method 900 proceeds to 912. At 912, method 900 includes enabling the stop-start functionality. As similarly described above in relation to 910, in one example, enabling the stop-start controller at 912 includes adjusting a state of the stop-start controller from a disabled state to an enabled state, while in other examples, the stop-start controller may already be in the enabled state, whereby enabling the stop-start controller at 912 includes continuing the enabled state of the stop-start controller. For example, the vehicle may travel through a first road segment that includes no stressful road attributes, followed by a second road segment that includes one or more stressful road attributes. When approaching the first road segment, the stop-start controller may be in an enabled state in accordance with method 900 due to a predicted low level of anxiety of the driver. As the vehicle approaches the second road segment, the stop-start controller may still be in the enabled state, and thus enabling the stop-start functionality includes continuing the enabled state of the stop-start controller.

As one example, the driver of the vehicle may be driving on a road segment that includes an intersection where the driver intends to turn left, a scenario that may produce stress in some drivers. Prior to approaching the intersection, the controller of the vehicle may retrieve an anxiety classification of the driver from a navigational database (e.g., the navigational database 450 of the neural network training system 400 of FIG. 4) based on upcoming road segment data and a driver classification retrieved from a driver database or determined by a driver classification model. The anxiety classification for the upcoming road segment may predict a high level of anxiety of the driver on the road segment. As a result of the predicted high level of anxiety of the driver, a routine executing on a processor of the controller may recommend that the stop-start control system of the vehicle be inhibited, to reduce the level of anxiety of the driver on the road segment. The recommendation may be inputted into the rule-based system to determine whether or not to selectively disable the stop-start control system. To determine whether or not to selectively disable the stop-start control system, the rule-based system may consider the recommendation along with sensor data from one or more vehicle sensors. Based on a logic of the rule-based system, the rule-based system may output to the controller an instruction to inhibit the stop-start controller based on the predicted high level of anxiety of the driver.

Figure 10:
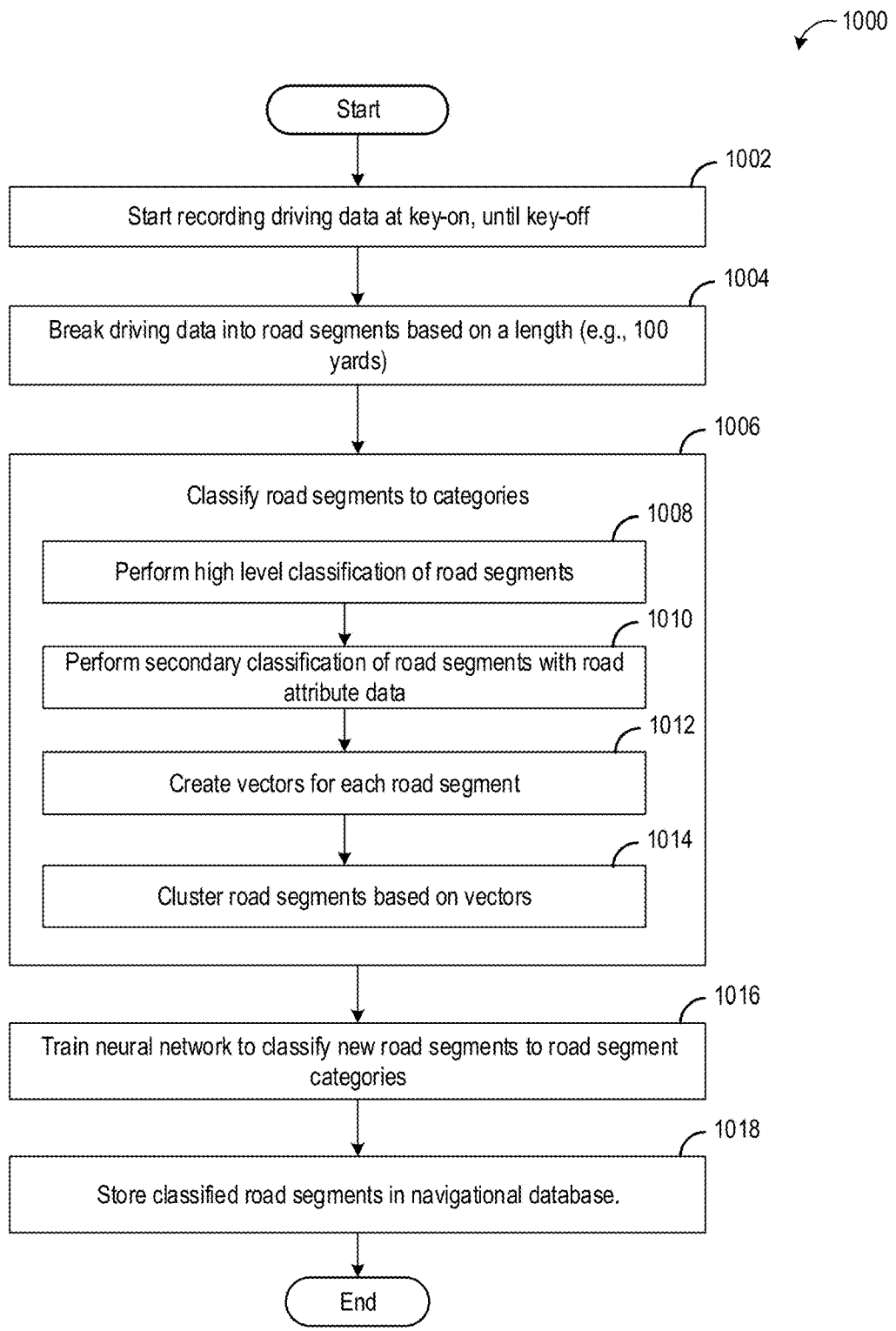
FIG. 10 shows a flow chart illustrating an example method for classifying road segments of a route.
Figure 11:
FIG. 11 shows a detection of an emotional state of a driver via a dashboard video camera, according to an exemplary embodiment.

Referring now to FIG. 10, an exemplary method 1000 is described for training a road segment classification model based on a neural network, such as the road segment classification model described in relation to the neural network training system 400 of FIG. 4. In one example, the road segment classification model is used to selectively inhibit an engine stop-start controller of a vehicle, as described above in method 500 of FIG. 5.

At 1002, method 1000 includes starting to record driving data of the vehicle at key-on, where recording of driving data is continued until key-off. In one example, the driving data includes driver performance data captured by internal vehicle sensors (e.g., the driver performance data 414 of the neural network training system 400 of FIG. 4) and road data captured by external vehicle sensors (e.g., the road segment data 418 of the neural network training system 400 of FIG. 4). At 1004, method 1000 includes breaking the driving data into road segments based on an average predetermined length. In one example, the predetermined length may be determined based on a distance range of the external vehicle sensors. For example, if a route of the vehicle includes straight sections of road on open land where the external vehicle sensors (e.g., a camera, radar, etc.) can capture data over a long distance, the predetermined length may be several hundred yards. Alternatively, if a route of the vehicle includes curved sections of road in a forested, hilly area where the external vehicle sensors cannot capture data over a long distance, the predetermined length may be shorter (e.g., 100 yards). In one example, the road segments have a minimum length (e.g., 100 yards) and a maximum length (e.g., a quarter mile). In some examples, the route of the vehicle may be divided into an exact number of road segments, while in other examples, the route of the vehicle may not be divided into an exact number of road segments, and a final road segment may be included that is less than the minimum length.

At 1006, method 1000 includes classifying the road segments to road segment categories. Classification of the road segments to road segment categories includes, at 1008, performing a high level classification of the road segments. For example, a road segment may be assigned a high level classification based on a general type of road (e.g., a highway, urban road, rural road, etc.). In one example, the classification is a numeric code (e.g., 01 for a highway, 02 for an urban road, etc.) At 1010, method 1000 includes performing a secondary classification of the road segments with road attribute data. During the secondary classification, the road segments are further classified based on one or more characteristics such as altitude, grade, curvature, physical attributes, sign attributes, presence of stoplights, proximity to other roads, traffic, etc. Similar to the high-level classification, numeric codes may be assigned to the road segments for each of the one or more characteristics (e.g., a numeric code for altitude, a numeric code for grade, etc.) Thus, as a result of performing the high level classification and the secondary classification of road segments, each road segment is characterized numerically in a manner that differentiates the road segment from other road segments.

At 1012, method 1000 includes creating vectors to represent each road segment. As described above, the data used to define the road segments may be coded as numeric values, where the road segments are represented as vectors comprising the numeric values. For example, each vector may include a numeric classification code corresponding to the high level classification performed at 1008, and additional numeric classification codes assigned during the secondary classification performed at 1010.

At 1014, method 1000 includes clustering the road segments based on the vectors created at 1012. In one example, a K-means clustering algorithm is used to determine a number n of natural categories of the road segments, for example, in the manner described above in reference to the construction of the driver classification model 314 of the engine start-stop control system 300 of FIG. 3).

At 1016, method 1000 includes training a neural network to classify new road segments to the road segment categories determined at 1012 by the clustering algorithm. The neural network may be the same as or similar to the neural network 402 of the neural network training system 400 of FIG. 4. During a training procedure, training and test data sets are compiled from the road segment vectors, and the neural network is trained to classify each road segment vector to the road segment category vector that the road segment vector is closest to. An error rate may be determined by a distance between the road segment category outputted by the neural network and a ground truth road segment category determined by the clustering algorithm. In one example, the difference is a Euclidean distance between the two vectors. The error rate may be back propagated through the layers of the neural network in order to adjust a plurality of weights and biases of a plurality of nodes of the neural network, until the neural network is able to classify the vectors into the road segment categories above a threshold accuracy (e.g., 95%).

At 1018, method 1000 includes storing the classified road segments in a navigational database (e.g., the navigational database 450 of the neural network training system 400 of FIG. 4). once the neural network has been trained and the vectors representing the road segments have been associated with road segment categories, the road segment—road segment category pairs may be stored in a navigational database, whereby additional data such as anxiety classification data may be associated with the road segment categories in the navigational database. Thus, as the vehicle encounters a new road segment, a controller of the vehicle may use the neural network to assign a road segment category to the new road segment, and then use the road segment category to retrieve the additional data associated with the road segment category from the navigational database.

In one example, the trained neural network is loaded into a memory of the vehicle (e.g., the memory 206 of control system 202 of FIG. 2), and during vehicle operation the trained neural network may be used to classify new road segments to one of the road segment categories generated at 1014. For example, a vehicle operating on a road segment may detect one or more road attributes, such as an intersection, a curvature of the road segment, etc. The vehicle may input the road segment with the one or more road attributes into the neural network to receive a road segment category of the road segment.

Thus, an example method for selectively inhibiting a stop-start controller of a vehicle based on a predicted level of anxiety of a driver includes collecting a first set of data on an emotional state of the driver via in-cabin sensors, while concurrently collecting a second set of data on a driving condition encountered by the vehicle via one or more remote sources and/or external sensors of the vehicle, and training a neural network to associate an emotion determined from the first set of data with the driving condition determined from the second set of data. Once trained, the neural network may be used to predict how the driver will respond emotionally, and in particular, whether the driver will experience an increased anxiety, upon the presentation of a similar driving condition in the future. If the driver is predicted to experience an increased anxiety related to the stop-start controller when the driver encounters a road attribute, the stop-start controller may be selectively inhibited, thereby reducing the anxiety of the driver.

In this way, by anticipating a future drive condition wherein the driver may experience anxiety when the vehicle has stopped, the anxiety of the driver may be reduced by inhibiting the stop-start functionality. Further, the navigation system may re-route the driver, or learn to map new routes to avoid situations that may create anxiety for the driver. An additional benefit of the systems and methods described herein is that by aggregating driver data and leveraging a connected vehicle architecture, long learning curves of prior architectures where individual driver data is collected over a long time period may be avoided. Further, by using a plurality of emotion detection models (visual, audio, physiological, etc.) concurrently, a more robust assessment of driver anxiety may be achieved than that which is provided by current models.

The technical effect of selectively inhibiting a stop-start control system of a vehicle based on a predicted level of anxiety of a driver is that an optimal strategy for managing an anxiety level of the driver may be devised that reduces anxiety provoked by road attributes on a route of the driver, while exploiting the fuel efficiency of selectively using the stop-start control system.

The disclosure also provides support for a method for a controller of a vehicle, comprising determining a driver classification for a driver operating the vehicle, predicting an anxiety level of the driver at an upcoming road segment, based on the driver classification, and selectively inhibiting an upcoming engine idle-stop event based on the predicted anxiety level of the driver. In a first example of the method, selectively inhibiting an upcoming engine idle-stop event includes inputting the predicted anxiety level of the driver into a rule-based system that determines whether to inhibit the upcoming engine idle-stop event based on the predicted anxiety level of the driver and an output of one or more vehicle sensors. In a second example of the method, optionally including the first example, the method further comprises determining the upcoming road segment from look-ahead road attribute information acquired via one or more of an external sensor of the vehicle, a radar system of the vehicle, a navigational system of the vehicle, a vehicle-to-vehicle network, and a remote server. In a third example of the method, optionally including the first and second examples, determining a driver classification includes inputting vehicle and driver performance data of the driver into a neural network trained to classify the driver into one of a plurality of driver categories. In a fourth example of the method, optionally including the first through third examples, the plurality of driver categories is determined by collecting driver performance data from a plurality of drivers, collecting vehicle data from the plurality of drivers, creating a plurality of vectors, where each vector of the plurality of vectors includes the driver performance and vehicle data of each driver of the plurality of drivers, and applying a clustering algorithm to the plurality of vectors to establish the plurality of driver categories. In a fifth example of the method, optionally including the first through fourth examples, predicting an anxiety level of the driver at the upcoming road segment includes using a trained neural network to classify the upcoming road segment to a road segment category, retrieving an anxiety classification of the road segment category from a database, where the anxiety classification is based on the driver classification. In a sixth example of the method, optionally including the first through fifth examples, the anxiety classification is an output of an anxiety classification model based on an output of an audio emotion detection model, an output of a facial emotion detection model, and an output of a physiological emotion detection model. In a seventh example of the method, optionally including the first through sixth examples, the audio emotion detection model takes as input audio information of a driver collected via a microphone installed inside a vehicle of the driver, the facial emotion detection model takes as input facial images of the driver collected via a camera installed inside the vehicle of the driver, and the physiological emotion detection model takes as input physiological data of the driver collected via an internet-of-things (TOT) device worn by the driver.

The disclosure also provides support for a method for a controller of a vehicle, comprising in a first condition, inhibiting an engine start-stop of the vehicle in response to a predicted high level of anxiety of a driver of the vehicle at a first upcoming road segment even if conditions indicate fuel savings by shutting off an engine of the vehicle, so that the engine is not shut off during vehicle operation on the first upcoming road segment, and in a second condition, stopping the engine of the vehicle in response to a predicted low level of anxiety of the driver at a second upcoming road segment and the conditions indicating fuel savings by shutting off the engine, so that the engine of the vehicle is shut off during vehicle operation on or before the second upcoming road segment, to save fuel. In a first example of the method, the predicted high level of anxiety of the driver of the vehicle at the first upcoming road segment is based on collecting data on road segments travelled from a plurality of drivers, collecting anxiety data from the plurality of drivers while travelling on the road segments, classifying the plurality of drivers into driver categories, classifying the data on road segments travelled into a plurality of road segment categories, classifying the anxiety data from the plurality of drivers to the driver categories, training a neural network to classify new road segments to a road segment category of the plurality of road segment categories, storing the road segment categories in a database, and for each road segment category of the plurality of road segment categories, constructing an anxiety classification model for each driver category from the anxiety data, associating the anxiety classification models for each driver category with the road segment categories in the database, retrieving the anxiety classification model corresponding to the driver category of the driver and the first upcoming road segment from the database, and predicting a level of anxiety of the driver based on an output of the anxiety classification model. In a second example of the method, optionally including the first example, collecting data on road segments travelled includes: dividing a route of a vehicle into a plurality of road segments, for each road segment, detecting one or more road attributes within the road segment via one or more of a sensor of the vehicle, a navigation system of the vehicle, and another vehicle via a vehicle-to-vehicle network, and associating the detected road attributes with the road segment. In a third example of the method, optionally including the first and second examples, collecting anxiety data from the plurality of drivers while travelling on the road segments includes, for each driver of the plurality of drivers, collecting audio information of the driver via a microphone installed inside a vehicle of the driver, collecting facial images of the driver via a camera installed inside the vehicle of the driver, and collecting physiological data of the driver via an internet-of-things (IOT) device worn by the driver. In a fourth example of the method, optionally including the first through third examples, collecting data from a plurality of drivers includes collecting, from each driver of the plurality of drivers, a pattern of neural activity from a portable ECG device worn by the driver, the pattern of neural activity to be used to establish ground truth anxiety classifications for training the anxiety classification model for each driver category. In a fifth example of the method, optionally including the first through fourth examples, the method further comprises: classifying the plurality of drivers into driver categories based on driver performance data collected from the plurality of drivers and vehicle data collected from the plurality of drivers.

The disclosure also provides support for a system for controlling an engine of a vehicle, comprising a stop-start controller of the engine of the vehicle, a controller with computer readable instructions stored on non-transitory memory that when executed during a driving condition, cause the controller to deploy a trained driver classification neural network to determine a driver category of a driver operating the vehicle, determine an upcoming road segment based on look-ahead road attribute information, deploy a trained road segment classification neural network to determine a road segment category of the upcoming road segment, retrieve an anxiety classification of the upcoming road segment for the driver category from an anxiety classification model associated with the driver category and the road segment category from a database, the driver of the vehicle classified into the driver category via a trained driver classification neural network, determine a predicted level of anxiety of the driver of the vehicle at the upcoming road segment, based on the anxiety classification, input the predicted level of anxiety of the driver of the vehicle into a rule-based system, and selectively enable or disable the stop-start controller of the engine of the vehicle based on an output of the rule-based system. In a first example of the system, the database includes a plurality of additional road segment categories, each road segment category including a plurality of driver categories, each driver category including a respective anxiety classification model. In a second example of the system, optionally including the first example, the instructions further cause the stop-start controller to be inhibited in response to the predicted level of anxiety of the driver, so that the engine remains on when one or more conditions are met that would otherwise trigger an idle-stop event. In a third example of the system, optionally including the first and second examples, the predicted level of anxiety of the driver of the vehicle is adjusted based on a level of anxiety of a second driver of a second vehicle in a network of vehicles, travelling on a route of the driver, where the second vehicle is ahead of the vehicle, and the level of anxiety of the second driver is transmitted to the vehicle via a vehicle-to-vehicle network. In a fourth example of the system, optionally including the first through third examples, the instructions further cause the controller to enter, as an additional input into the rule-based system, an output of a sensor of the vehicle. In a fifth example of the system, optionally including the first through fourth examples, the instructions further cause the controller to inhibit the stop-start controller in response to a first predicted anxiety of the driver on a first road segment, and, responsive to a second predicted anxiety on a second road segment, enable the stop-start controller so that the engine is shut down in response to idle-stop conditions being met.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations, and/or functions may be repeatedly performed depending on the particular strategy being used. Further, the described actions, operations, and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. Moreover, unless explicitly stated to the contrary, the terms "first," "second," "third," and the like are not intended to denote any order, position, quantity, or importance, but rather are used merely as labels to distinguish one element from another. The subject matter of the present disclosure includes all novel and non-obvious combinations and sub-combinations of the various systems and configurations, and other features, functions, and/or properties disclosed herein.

As used herein, the term "approximately" is construed to mean plus or minus five percent of the range unless otherwise specified.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for a controller of a vehicle, comprising:
    determining a driver classification for a driver operating the vehicle;
    predicting a future anxiety level of the driver at an upcoming road segment, based on the driver classification, including classifying the upcoming road segment to a road segment category, and retrieving a stored anxiety classification of the road segment category from a database, where the stored anxiety classification is based on the driver classification; and
    selectively inhibiting an upcoming engine idle-stop event based on the predicted anxiety level of the driver.

2. The method of claim 1, wherein selectively inhibiting an upcoming engine idle-stop event includes inputting the predicted future anxiety level of the driver into a rule-based system that determines whether to inhibit the upcoming engine idle-stop event based on the predicted future anxiety level of the driver and an output of one or more vehicle sensors.

3. The method of claim 1, further comprising determining the upcoming road segment from look-ahead road attribute information acquired via one or more of an external sensor of the vehicle, a radar system of the vehicle, a navigational system of the vehicle, a vehicle-to-vehicle network, and a remote server.

4. The method of claim 1, wherein determining a driver classification includes inputting vehicle and driver performance data of the driver into a neural network trained to classify the driver into one of a plurality of driver categories.

5. The method of claim 4, wherein the plurality of driver categories is determined by:
    collecting driver performance data from a plurality of drivers;
    collecting vehicle data from the plurality of drivers;
    creating a plurality of vectors, where each vector of the plurality of vectors includes the driver performance and vehicle data of each driver of the plurality of drivers; and
    applying a clustering algorithm to the plurality of vectors to establish the plurality of driver categories.

6. The method of claim 1, wherein predicting future anxiety level of the driver at the upcoming road segment includes:
    using a trained neural network to classify the upcoming road segment to the road segment category.

7. The method of claim 6, wherein the anxiety classification is an output of an anxiety classification model based on an output of an audio emotion detection model, an output of a facial emotion detection model, and an output of a physiological emotion detection model.

8. The method of claim 7, wherein:
    the audio emotion detection model takes as input audio information of a driver collected via a microphone installed inside a vehicle of the driver;
    the facial emotion detection model takes as input facial images of the driver collected via a camera installed inside the vehicle of the driver; and
    the physiological emotion detection model takes as input physiological data of the driver collected via an internet-of-things (IOT) device worn by the driver.

9. A method for a controller of a vehicle, comprising:
    in a first condition, inhibiting an engine start-stop of the vehicle in response to a predicted high future level of anxiety of a driver of the vehicle at a first upcoming road segment even if conditions indicate fuel savings by shutting off an engine of the vehicle, so that the engine is not shut off during vehicle operation on the first upcoming road segment; and
    in a second condition, stopping the engine of the vehicle in response to a predicted low future level of anxiety of the driver at a second upcoming road segment and the conditions indicating fuel savings by shutting off the engine, so that the engine of the vehicle is shut off during vehicle operation on or before the second upcoming road segment, to save fuel.

10. The method of claim 9, wherein the predicted high level of anxiety of the driver of the vehicle at the first upcoming road segment is based on:

collecting data on road segments travelled from a plurality of drivers;

collecting anxiety data from the plurality of drivers while travelling on the road segments;

classifying the plurality of drivers into driver categories;

classifying the data on road segments travelled into a plurality of road segment categories;

classifying the anxiety data from the plurality of drivers to the driver categories;

training a neural network to classify new road segments to a road segment category of the plurality of road segment categories;

storing the road segment categories in a database;

for each road segment category of the plurality of road segment categories, constructing an anxiety classification model for each driver category from the anxiety data;

associating the anxiety classification models for each driver category with the road segment categories in the database;

retrieving the anxiety classification model corresponding to the driver category of the driver and the first upcoming road segment from the database; and predicting a level of anxiety of the driver based on an output of the anxiety classification model.

11. The method of claim 10, wherein collecting data on road segments travelled includes: dividing a route of a vehicle into a plurality of road segments;

for each road segment, detecting one or more road attributes within the road segment via one or more of a sensor of the vehicle, a navigation system of the vehicle, and another vehicle via a vehicle-to-vehicle network; and associating the detected road attributes with the road segment.

12. The method of claim 10, wherein collecting anxiety data from the plurality of drivers while travelling on the road segments includes, for each driver of the plurality of drivers:

collecting audio information of the driver via a microphone installed inside a vehicle of the driver;

collecting facial images of the driver via a camera installed inside the vehicle of the driver; and collecting physiological data of the driver via an internet-of-things (IOT) device worn by the driver.

13. The method of claim 10, wherein collecting data from a plurality of drivers includes collecting, from each driver of the plurality of drivers, a pattern of neural activity from a portable ECG device worn by the driver, the pattern of neural activity to be used to establish ground truth anxiety classifications for training the anxiety classification model for each driver category.

14. The method of claim 10, further comprising classifying the plurality of drivers into driver categories based on driver performance data collected from the plurality of drivers and vehicle data collected from the plurality of drivers.

15. A system for controlling an engine of a vehicle, comprising:

a stop-start controller of the engine of the vehicle;

a controller with computer readable instructions stored on non-transitory memory that when executed during a driving condition, cause the controller to:

deploy a trained driver classification neural network to determine a driver category of a driver operating the vehicle;

determine an upcoming road segment based on look-ahead road attribute information;

deploy a trained road segment classification neural network to determine a road segment category of the upcoming road segment;

retrieve an anxiety classification of the upcoming road segment for the driver category from an anxiety classification model associated with the driver category and the road segment category from a database, the driver of the vehicle classified into the driver category via a trained driver classification neural network;

determine a predicted future level of anxiety of the driver of the vehicle at the upcoming road segment, based on the anxiety classification;

input the predicted future level of anxiety of the driver of the vehicle into a rule-based system; and selectively enable or disable the stop-start controller of the engine of the vehicle based on an output of the rule-based system.

16. The system of claim 15, wherein the database includes a plurality of additional road segment categories, each road segment category including a plurality of driver categories, each driver category including a respective anxiety classification model.

17. The system of claim 15, wherein the instructions further cause the stop-start controller to be inhibited in response to the predicted future level of anxiety of the driver, so that the engine remains on when one or more conditions are met that would otherwise trigger an idle-stop event.

18. The system of claim 15, wherein the predicted future level of anxiety of the driver of the vehicle is adjusted based on a level of anxiety of a second driver of a second vehicle in a network of vehicles, travelling on a route of the driver, where the second vehicle is ahead of the vehicle, and the level of anxiety of the second driver is transmitted to the vehicle via a vehicle-to-vehicle network.

19. The system of claim 15, wherein the instructions further cause the controller to enter, as an additional input into the rule-based system, an output of a sensor of the vehicle.

20. The system of claim 15, wherein the instructions further cause the controller to inhibit the stop-start controller in response to a first predicted anxiety of the driver on a first road segment, and, responsive to a second predicted anxiety on a second road segment, enable the stop-start controller so that the engine is shut down in response to idle-stop conditions being met.

* * * * *